(12) United States Patent
Lynn et al.

(10) Patent No.: US 9,400,244 B2
(45) Date of Patent: Jul. 26, 2016

(54) IMMOBILIZATION OF DROPLETS OF LIQUID CRYSTALS ON SURFACES

(75) Inventors: David M. Lynn, Middleton, WI (US);
Nicholas L. Abbott, Madison, WI (US);
Maren E. Buck, Pasadena, CA (US);
Michael I. Kinsinger, Pleasanton, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1395 days.

(21) Appl. No.: 13/087,667

(22) Filed: Apr. 15, 2011

(65) Prior Publication Data

US 2011/0306142 A1    Dec. 15, 2011

Related U.S. Application Data

(60) Provisional application No. 61/324,650, filed on Apr. 15, 2010.

(51) Int. Cl.
| | |
|---|---|
| *G01N 31/00* | (2006.01) |
| *G01N 31/22* | (2006.01) |
| *G01N 21/78* | (2006.01) |
| *G01N 21/05* | (2006.01) |
| *G01N 21/21* | (2006.01) |
| *G01N 21/77* | (2006.01) |
| *G01N 33/44* | (2006.01) |

(52) U.S. Cl.
CPC ............. *G01N 21/21* (2013.01); *G01N 21/77* (2013.01); *G01N 31/00* (2013.01); *G01N 31/22* (2013.01); *G01N 33/442* (2013.01); *Y10T 428/24802* (2015.01)

(58) Field of Classification Search
CPC ..... G01N 33/442; G01N 31/00; G01N 31/22; G01N 21/3563; G01N 33/92; G01N 2800/044; G01N 33/6893; G01N 2800/32; G01N 21/8483; G01N 21/78; G01N 21/05; G01N 21/553; G01N 33/54373; C08F 10/00; C12Q 1/60
USPC .................................... 436/85, 71; 422/82.05
See application file for complete search history.

(56) References Cited

U.S. PATENT DOCUMENTS

| | | | |
|---|---|---|---|
| 6,284,197 B1 * | 9/2001 | Abbott ................... | G01N 21/75 422/412 |
| 2009/0023155 A1 * | 1/2009 | Abbott et al. .................. | 435/7.1 |

OTHER PUBLICATIONS

Dynamic Ordering Transitions of Liquid Crystals Driven by Interfacial Complexes Formed between Polyanions and Amphiphilic Polyamines Michael I. Kinsinger, Maren E. Buck, Fernando Campos, David M. Lynn, and Nicholas L. Abbott Langmuir, vol. 24, No. 23, 2008.*

(Continued)

*Primary Examiner* — Krishnan S Menon
*Assistant Examiner* — Dwan A Gerido
(74) *Attorney, Agent, or Firm* — Boyle Fredrickson S.C.

(57) ABSTRACT

Devices and methods for immobilizing micrometer sized liquid domains onto a chemically functionalized substrate surface are disclosed. A multifunctional polymer is adsorbed at the surface interface of the liquid microdomains, and the liquid microdomains are immobilized by covalent bonding or non-covalent forces such as electrostatic attraction between the adsorbed multifunctional polymer and the functionalized substrate surface.

22 Claims, 11 Drawing Sheets

(56) References Cited

OTHER PUBLICATIONS

Layer by Layer Assembly of Reactive Ultrathin Films Mediated by Click Type Reactions of Poly(2-Alkenyl Azlactone)s Maren E. Buck, Jingtao Zhang, David M. Lynn Adv. Mater. 2007, 19, 3951-3955.*

Abbott N. L. , "Preparation of microscopic and planar oil-water interfaces that are decorated with prescribed densities of insoluble amphiphiles" (2008) J. Am. Chem. Soc. 130, 4326-33.

Brake, J. M., et al., "Effect of Surfactant Structure on the Orientation of Liquid Crystals at Aqueous-Liquid Crystal Interfaces" (2003) Langmuir 19, 6436-6442.

Brake, J.M., et al., "Coupling of the orientations of thermotropic liquid crystals to protein binding events at lipid-decorated interfaces" (2007) Langmuir 23, 8497-507.

Breitbach, A. S., et al., "Chemical modification of reactive multilayered films fabricated from poly(2-alkenyl azlactone)s: design of surfaces that prevent or promote mammalian cell adhesion and bacterial biofilm growth" (2009) Biomacromolecules 10, 1564-74.

Buck, M. E., et al. "Layer-by-Layer Assembly of Reactive Ultrathin Films Mediated by Click-Type Reactions of Poly(2-Alkenyl Azlactone)s" (2007) Adv. Mater. 19, 3951-3955.

Drzaic, P. S., Liquid Crystal Dispersions. World Scientific Publishing Co.: Singapore, 1995 pp. 17-39.

Guichard, B., et al., "Reactive poly(2-vinyl-4,4-dimethyl-5-oxazoione) and poly[(2-vinyl-4,4-dimethyl-5-oxazolone)-co-(methyl methacrylate)]s. Synthesis, characterization and chemical modification with 4-methoxy-4'-(β-aminoethoxy) biphenyl" (1998) Macromol. Chem. Phys. 199, 1657-1674.

Gupta, J. K., et al., "Size-dependent ordering of liquid crystals observed in polymeric capsules with micrometer and smaller diameters" (2009) Angew. Chem., Int. Ed. 48, 1652-5.

Gupta, J. K., et al., "Characterization of adsorbate-induced ordering transitions of liquid crystals within monodisperse droplets" (2009) Langmuir 25, 9016-24.

Kinsinger, M. I., et al., "Dynamic ordering transitions of liquid crystals driven by interfacial complexes formed between polyanions and amphiphilic polyamines" (2008) Langmuir 24, 13231-6.

Kinsinger, M. I., et al., "Langmuir films of flexible polymers transferred to aqueous/liquid crystal interfaces induce uniform azimuthal alignment of the liquid crystal" (2010) J. Colloid Interface Sci. 341, 124-35.

Kuroda, et al., "Amphiphilic polymethacrylate derivatives as antimicrobial agents" (2005) J. Am. Chem. Soc. 127, 4128-9.

Liu, X. H., et al., "Charge-Shifting Cationic Polymers That Promote Self-Assembly and Self-Disassembly with DNA" (2005) Macromolecules 38, 7907-7914.

Park, J. S., et al., "Ordering Transitions in Thermotropic Liquid Crystals Induced by the Interfacial Assembly and Enzymatic Processing of Oligopeptide Amphiphiles" (2008) Adv. Mater. 20, 1185-1190.

Price, A. D., et al., "DNA hybridization-induced reorientation of liquid crystal anchoring at the nematic liquid crystal/aqueous interface" (2008) J. Am. Chem. Soc. 130, 8188-94.

Sivakumar, S., et al., "Monodisperse Emulsions through Templating Polyelectrolyte Multilayer Capsules" (2008) Chem. Mater. 20(6), 2063-2065.

Sivakumar, S., et al., "Liquid Crystal Emulsions as the Basis of Biological Sensors for the Optical Detection of Bacteria and Viruses" (2009) Adv. Funct. Mater. 19, 2260-2265.

Tanaka, R., et al., "High molecular weight linear polyethylenimine and poly(N-methylethylenimine)" (1983) Macromolecules 16, 849-853.

* cited by examiner

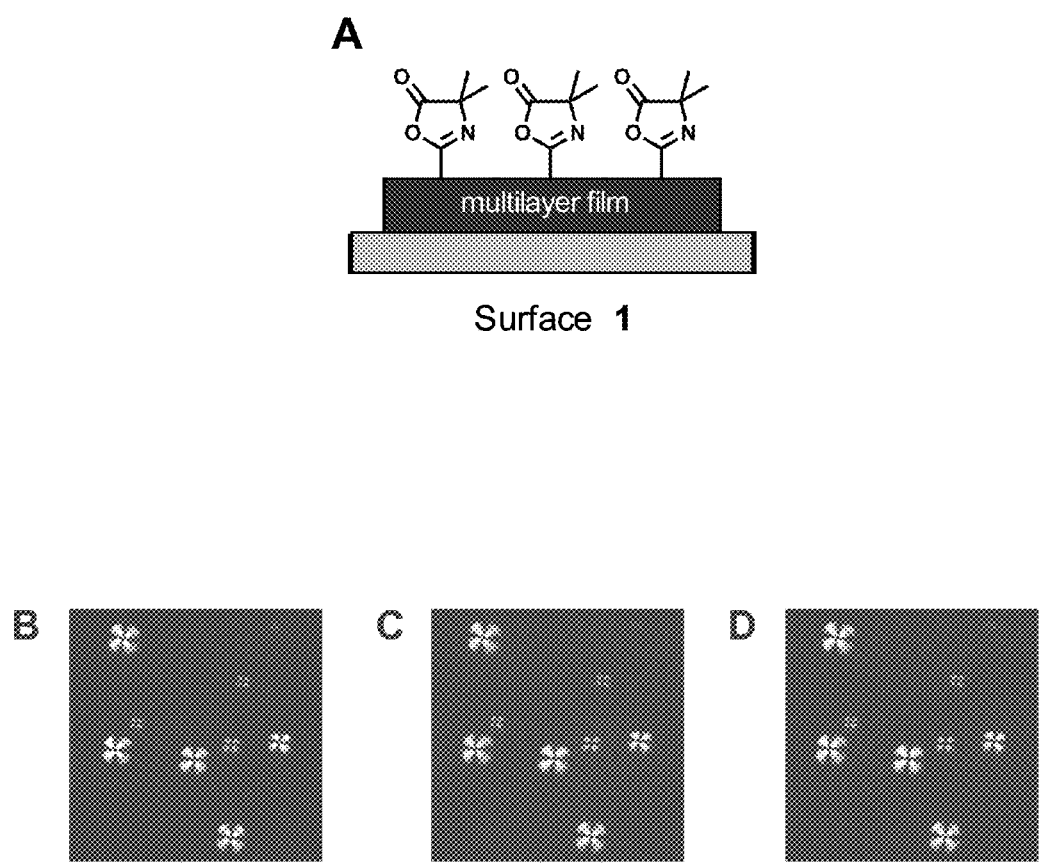
FIGURE 3A-D

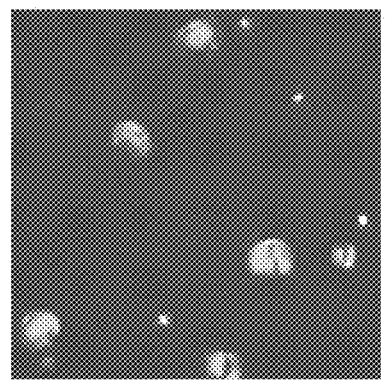 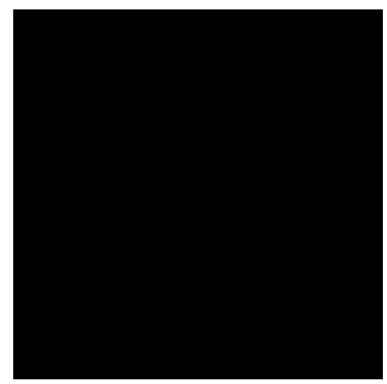
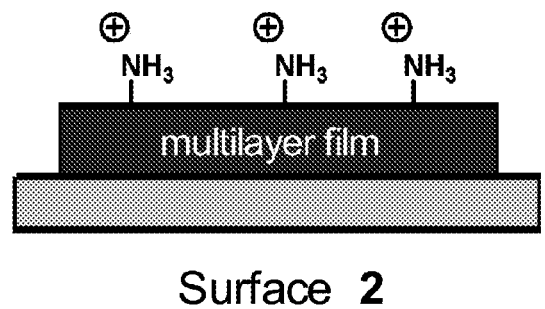
FIGURE 3E-G

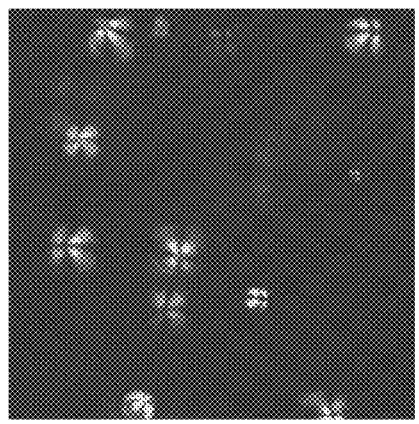 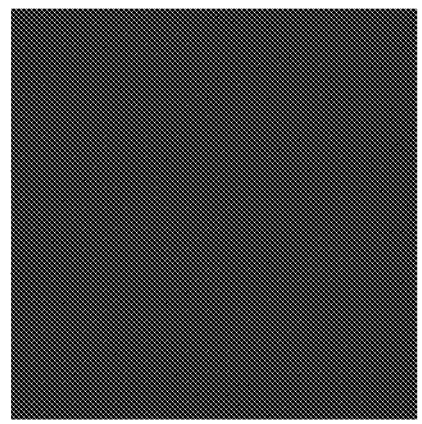
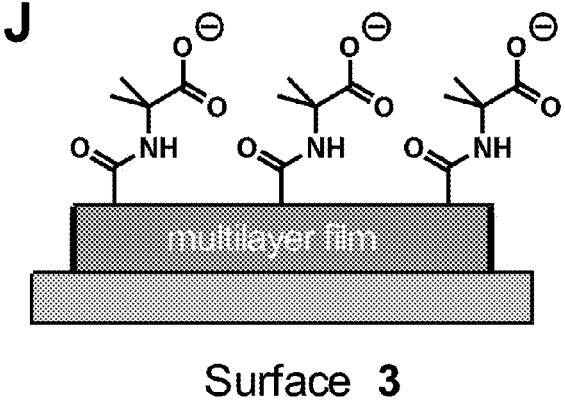
FIGURE 3H-J

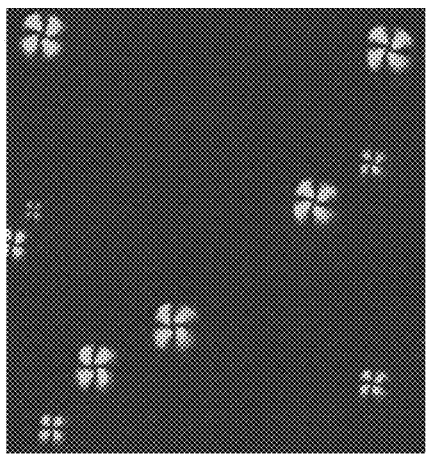
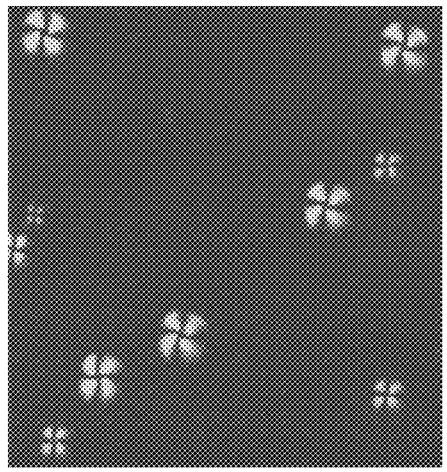
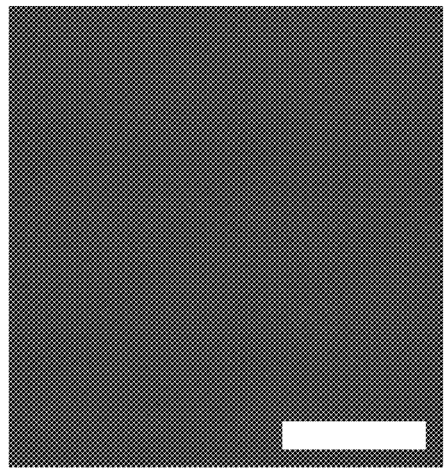
FIGURE 3K-M

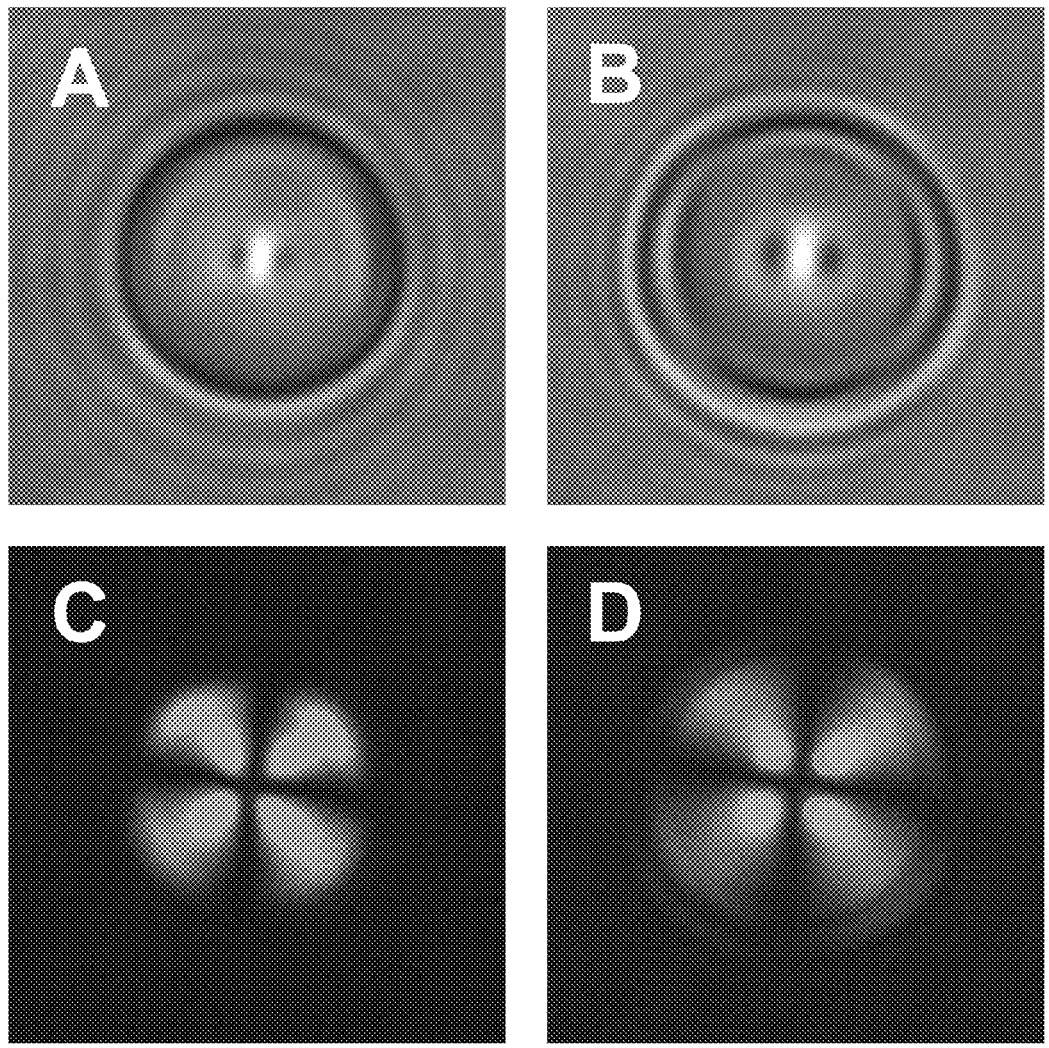
FIGURE 5A-D

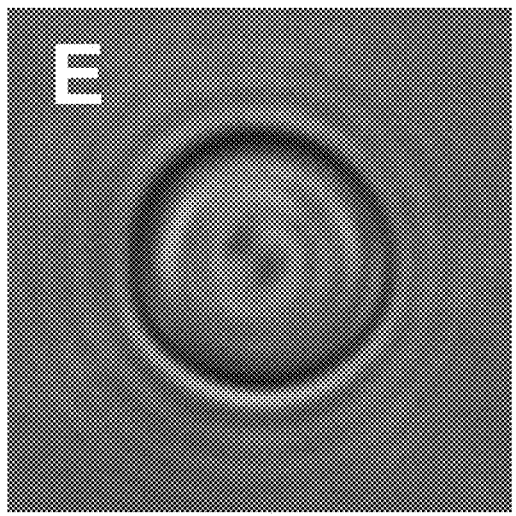
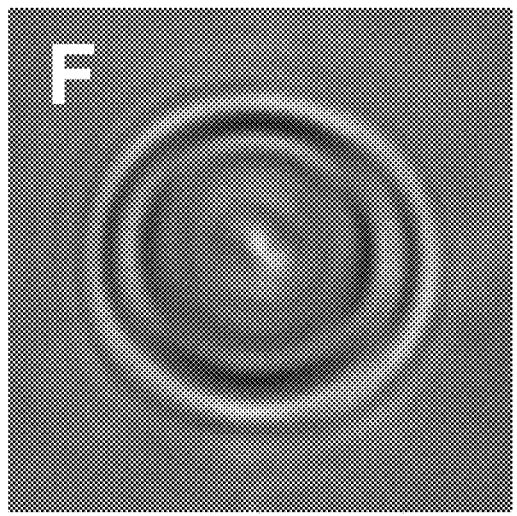
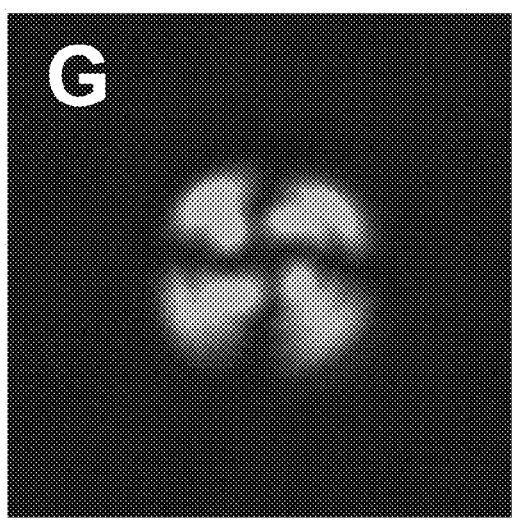
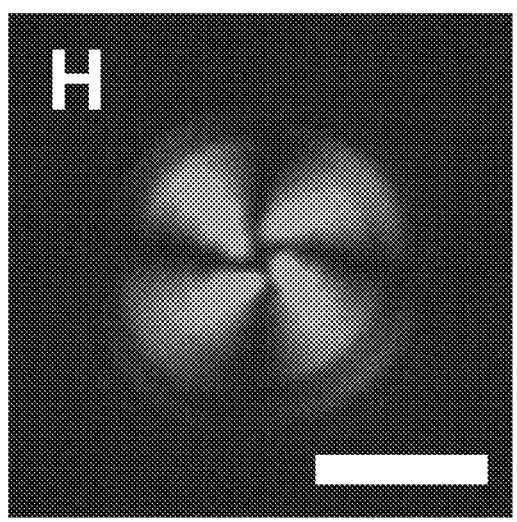
FIGURE 5E-H

IMMOBILIZATION OF DROPLETS OF LIQUID CRYSTALS ON SURFACES

CROSS-REFERENCE TO RELATED APPLICATIONS

This application claims the benefit of U.S. Provisional Application No. 61/324,650, filed on Apr. 15, 2010, which is incorporated by reference herein in its entirety.

STATEMENT REGARDING FEDERALLY SPONSORED RESEARCH OR DEVELOPMENT

This invention was made with government support under 0520527 awarded by the National Science Foundation. The government has certain rights in the invention.

FIELD OF THE INVENTION

This invention relates generally to structures comprising liquid droplets. In particular, the present invention is directed to structures and methods of polymer-facilitated immobilization of liquid crystal droplets on chemically functionalized solid surfaces.

BACKGROUND OF THE INVENTION

The orientational ordering of liquid crystals (LCs) is exceptionally sensitive to the structures and properties of surfaces or interfaces with which they are in contact. Because changes in the orientation of LCs can propagate over large distances (e.g., up to tens of micrometers) through the bulk, changes in the properties of LC interfaces that lead to small perturbations in orientation can be amplified and observed readily using polarized-light. This aspect of LC-based systems has been exploited to develop new sensing platforms that can report on the presence and/or organization of chemical or biological agents.

For example, several recent studies have demonstrated that ordering transitions in LCs can be triggered by the adsorption of phospholipids (Abbott, N. L. J. Am. Chem. Soc. 2008, 130, 4326; Brake, J. M.; Abbott, N. L. Langmuir 2007, 23, 8497), surfactants (Brake, J. M.; Mezera, A. D.; Abbott, N. L. Langmuir 2003, 19, 6436), polymers (Price, A. D.; Schwartz, D. K. J. Am. Chem. Soc. 2008, 130, 8188; Kinsinger, M. I.; Buck, M. E.; Campos, F.; Lynn, D. M.; Abbott, N. L. Langmuir 2008, 24, 13231), proteins (Park, J. S.; Abbott, N. L. Adv. Mater. 2008, 20, 1185), and viruses and bacteria (Sivakumar, S.; Wark, K. L.; Gupta, J. K.; Abbott, N. L.; Caruso, F. Adv. Funct. Mater. 2009, 19, 2260) at interfaces created between LCs and solid substrates or LCs and aqueous phases. The results of these past studies have suggested new principles and approaches for the design of LC-based systems that have relevance in a broad range of fundamental and applied contexts (e.g., sensing).

Past studies on the behavior of aqueous/LC interfaces have focused, in large measure, on the design and investigation of interfaces that are approximately planar (for example, interfaces formed by creating a thin film of a thermotropic LC between a solid substrate and a bulk aqueous phase) (Lockwood, N. A.; Gupta, J. K.; Abbott, N. L. Surf. Sci. Rep. 2008, 63, 255). In these experimental systems, planar solid substrates are used to provide a physical support for thin films of LC and as a means to define or control the orientation of the LC at one boundary.

It has been shown that amphiphilic polymers can assemble at planar aqueous/LC interfaces in ways that trigger ordering transitions in the LCs, and studies have also demonstrated that it is possible to design polymers and polymer-decorated LC interfaces that respond to external stimuli (e.g., changes in the pH of the aqueous phase or the presence of oppositely-charged polyelectrolytes) (Kinsinger, M. I.; Buck, M. E.; Meli, M. V.; Abbott, N. L.; Lynn, D. M. J. Colloid Interface Sci. 2010, 341, 124).

An alternative geometry that has recently been explored involves the use of LC droplets dispersed in a continuous aqueous phase (Gupta, J. K.; Zimmerman, J. S.; de Pablo, J. J.; Caruso, F.; Abbott, N. L. Langmuir 2009, 25, 9016). This approach has the advantage that surface treatment of solid substrates is not required to define the orientation of the LC. Several past studies have demonstrated that the interfaces of LC emulsion droplets can be decorated by the spontaneous adsorption of surfactants or phospholipids, and that these interfaces can be tailored to drive ordering transitions involving topological defects that are induced by the spherical geometries (Gupta, J. K.; Sivakumar, S.; Caruso, F.; Abbott, N. L. Angew. Chem., Int. Ed. 2009, 48, 1652). In addition to eliminating the need for solid substrates, as noted above, the confinement of the LC into spherical geometries offers new approaches to manipulate the ordering of the LCs (Drzaic, P. S., Liquid Crystal Dispersions. World Scientific Publishing Co.: Singapore, 1995).

For example, the ordering of LCs confined within droplets is sensitive to the size of the droplets, thereby providing additional means to tune the response of the LC (e.g., ordering transitions) to interfacial events by controlling droplet size (Gupta, J. K.; Sivakumar, S.; Caruso, F.; Abbott, N. L. Angew. Chem., Int. Ed. 2009, 48, 1652). In this context, past studies have described methods to encapsulate LC droplets dispersed in aqueous media based on the assembly of water-soluble polymers at the interfaces of the droplets (Sivakumar, S.; Gupta, J. K.; Abbott, N. L.; Caruso, F. Chem. Mater. 2008, 20(6), 2063-2065).

However, in the case of non-planar LC aqueous interfaces such as those characteristic of LC dispersions, a complicating factor is the ability of the droplets to move freely within the surrounding medium. While a high level of droplet mobility can be desirable in certain contexts, it can also create substantial challenges with respect to the characterization of individual LC droplets and any functions associated with the characterization of such droplets, such as droplet-based sensing.

SUMMARY OF THE INVENTION

The inventors have here demonstrated the immobilization of LC microdomains on solid surfaces facilitated by the adsorption of a multifunctional polymer at the interface of the microdomains and the surrounding material. The solid surfaces are chemically functionalized to immobilize the microdomains by covalent bonding or non-covalent interactions, such as electrostatic attractions. Immobilized liquid crystal microdomains would have utility in, as non-limiting examples, liquid crystal droplet-based sensing devices and devices engineered to possess optical band gaps. Accordingly, the invention encompasses devices having liquid crystal microdomains that are immobilized onto a solid surface, methods of making such devices, methods of using such devices, and methods of immobilizing liquid crystal microdomains onto a solid surface.

In a first aspect, the invention encompasses an immobilized liquid-based device. The device includes one or more liquid microdomains having a minor axis of between about 0.5 µm and about 1000 µm. The liquid microdomains incorporate a multifunctional polymer that facilitates the immobilization of the microdomains on a substrate surface.

The substrate surface on which the microdomains are immobilized is also part of the device. The microdomains are immobilized by one or both of a covalent bond or a non-covalent attraction between the multifunctional polymer and the substrate surface.

In certain preferred embodiments, the liquid microdomains have a minor axis of between about 0.5 µm and about 200 µm; more preferably, they have a minor axis of between about 0.5 µm and about 10 µm.

The liquid microdomains are preferably made of isotropic oils or liquid crystal. In certain embodiments, the liquid microdomains are liquid crystal droplets. In some such embodiments, the liquid crystal droplets are immobilized within an aqueous-liquid crystal emulsion.

As described in more detail in the detailed description below, a wide range of polymers can be selected for use as the multifunctional polymer. In certain embodiments, the multifunctional polymer is a polyamine. The polyamine optionally includes a side chain functionalized with a primary amine, and may further include a side chain terminating with an aliphatic alkyl moiety of at least five carbons in length. A preferred multifunctional polyamine polymer is the polymer having the chemical structure:

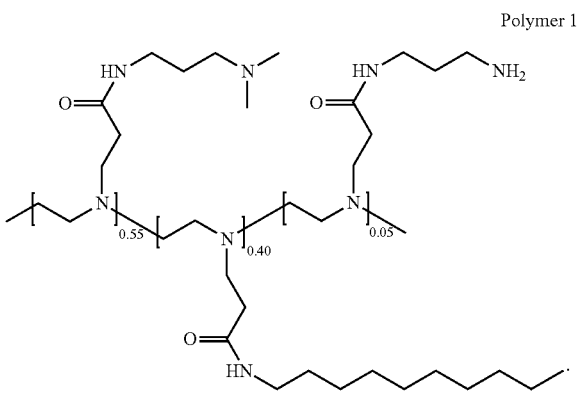

Polymer 1

In certain embodiments, the substrate surface of the device comprises a chemical functionalization layer to facilitate the immobilization of the liquid microdomains onto the substrate surface. Optionally, the immobilized liquid microdomains may form a pattern corresponding to the spatial placement of the chemical functionalization layer or components thereof. Methods of controlling the spatial placement of a chemical functionalization layer or components thereof are known in the art, and include without limitation patterning by printing, photolithography, lithography (including dip-pen lithography), contact printing, spotting, and spraying. In some embodiments that include a chemical functionalization layer, the substrate surface is a solid surface coated with a chemically functionalized polymer multilayer. The chemically functionalized polymer multilayer may optionally be functionalized by one or more of a terminal azlactone moiety, a terminal carboxylic acid moiety, or a terminal carboxylate moiety. Further, the outermost layer of the chemically functionalized polymer multilayer may optionally be fabricated to cover less than the entire substrate surface, and may form a pattern that corresponds to the pattern of the immobilized microdomains.

In certain embodiments wherein the substrate surface is coated with a chemically functionalized polymer multilayer, the multilayer is made up of one or more bilayers. In some such embodiments, the one or more bilayers are fabricated using poly(2-vinyl-4,4'-dimethylazlactone) and branched poly(ethylene imine), and the outermost layer is fabricated using poly(2-vinyl-4,4'-dimethylazlactone). Optionally, the azlactone moieties of the outermost poly(2-vinyl-4,4'-dimethylazlactone) layer are hydrolyzed to carboxylic acid or carboxylate moieties.

In some embodiments, a covalent bond is formed between the multifunctional polymer and the chemically functionalized polymer multilayer. Optionally, the multifunctional polymer may includes a side chain functionalized with a primary amine, and the substrate surface includes a chemically functionalized polymer multilayer having a terminal azlactone moiety. In such embodiments, the covalent bond is formed between the primary amine and the terminal azlactone moiety. In certain such embodiments, the multifunctional polymer is the polymer having the chemical structure:

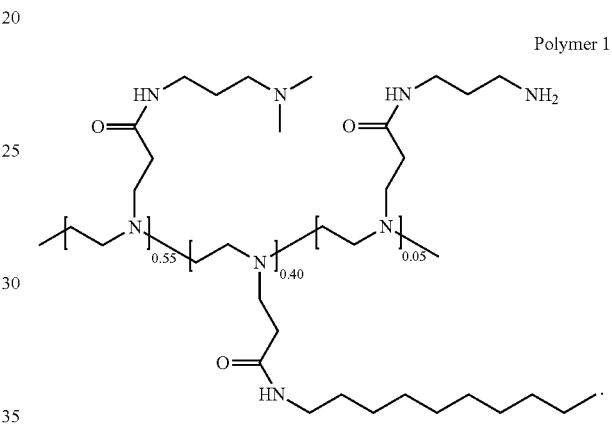

Polymer 1

In yet other embodiments, an electrostatic attraction is formed between the multifunctional polymer and the chemically functionalized polymer multilayer. In some such embodiments, a chemically functionalized polymer multilayer on the substrate surface includes a terminal carboxylic acid or carboxylate moiety. In certain such embodiments, the multifunctional polymer is the polymer having the chemical structure:

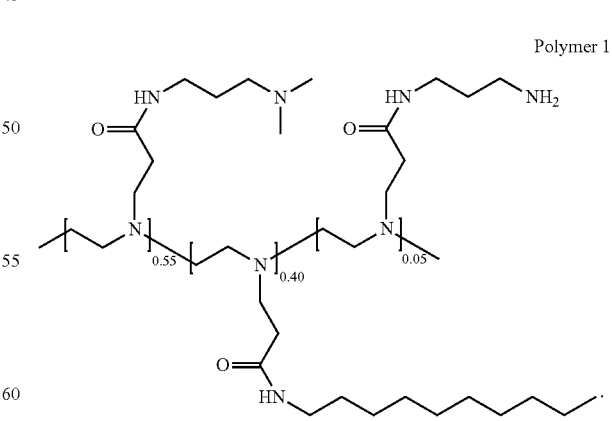

Polymer 1

In a second aspect, the invention encompasses a method of immobilizing liquid microdomains on a substrate surface. The method includes the steps of (a) coating a solid surface with a chemical functionalization layer to form a substrate surface; and (b) contacting one or more liquid microdomains with the substrate surface. The microdomains have a minor axis of between about 0.5 μm and about 1000 μm and further incorporate a multifunctional polymer. The microdomains are subsequently immobilized on the substrate surface.

In some embodiments, the microdomains are made of a liquid crystal or an isotropic oil. In certain such embodiments, the microdomains are comprised of liquid crystal, and the step of contacting the microdomains with the substrate surface is performed by contacting the substrate surface with an aqueous-liquid crystal emulsion containing the liquid crystal microdomains.

In some embodiments, the multifunctional polymer is a polyamine, which optionally can include a side chain functionalized with a primary amine and/or a side chain terminating with an aliphatic alkyl moiety of at least five carbons in length. In certain such embodiments, the polyamine polymer is the polymer having the chemical formula:

Polymer 1

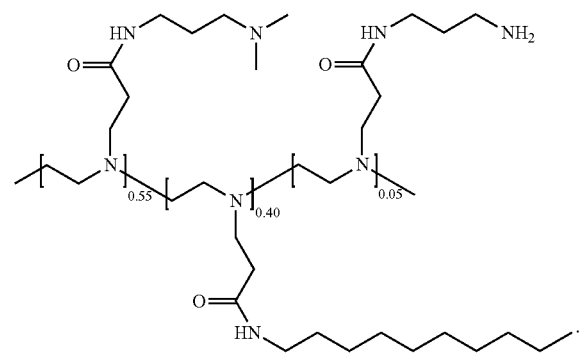

In certain embodiments, the chemical functionalization layer of the substrate surface is functionalized by one or more of a terminal azlactone moiety, a terminal carboxylic acid moiety, or a terminal carboxylate moiety.

Optionally, the chemical functionalization layer or components thereof may form a pattern on the solid surface, and the method includes the step of forming such a pattern. Methods of forming such patterns are known in the art, and include without limitation patterning by printing, photolithography, lithography (including dip-pen lithography), contact printing, spotting, and spraying. In certain embodiments, the chemical functionalization layer is a polymer multilayer. Optionally, the outermost layer is fabricated to cover less than the entire substrate surface and may form a particular pattern. In some such embodiments, the step of coating the solid surface with a chemical functionalization layer includes sequentially fabricating one or more bilayers over the solid surface. Optionally, the outermost layer has a terminal azlactone moiety. In certain preferred embodiments, the one or more bilayers are fabricated using poly(2-vinyl-4,4'-dimethylazlactone) and branched poly(ethylene imine), and the outermost layer is fabricated using poly(2-vinyl-4,4'-dimethylazlactone).

The step of coating the solid surface with a chemical functionalization layer may additionally include the step of hydrolyzing the azlactone moieties of the outermost layer to carboxylic acid or carboxylate moieties. A preferred way to perform this step is by exposing the outermost layer to water vapor.

In a third aspect, the invention encompasses a method of making an immobilized liquid-based device. The method includes the steps of (a) coating a solid surface with a chemical functionalization layer to form a substrate surface; and (b) contacting one or more liquid microdomains with the substrate surface. The microdomains have a minor axis of between about 0.5 μm and about 1000 μm and further incorporate a multifunctional polymer. The microdomains are subsequently immobilized on the substrate surface.

In some embodiments, the microdomains are made of a liquid crystal or an isotropic oil. In certain such embodiments, the microdomains are comprised of liquid crystal, and the step of contacting the microdomains with the substrate surface is performed by contacting the substrate surface with an aqueous-liquid crystal emulsion containing the liquid crystal microdomains.

In some embodiments, the multifunctional polymer is a polyamine, which optionally can include a side chain functionalized with a primary amine and/or a side chain terminating with an aliphatic alkyl moiety of at least five carbons in length. In certain such embodiments, the polyamine polymer is the polymer having the chemical formula:

Polymer 1

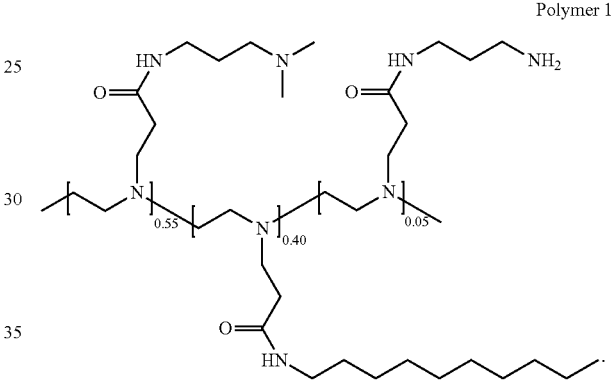

Optionally, the chemical functionalization layer or components thereof may form a pattern on the solid surface, and the method includes the step of forming such a pattern. Methods of forming such patterns are known in the art, and include without limitation patterning by printing, photolithography, lithography (including dip-pen lithography), contact printing, spotting, and spraying. In certain embodiments, the chemical functionalization layer of the substrate surface is functionalized by one or more of a terminal azlactone moiety, a terminal carboxylic acid moiety, or a terminal carboxylate moiety.

In certain embodiments, the chemical functionalization layer is a polymer multilayer. Optionally, the outermost layer is fabricated to cover less than the entire substrate surface and may form a particular pattern. In some such embodiments, the step of coating the solid surface with a chemical functionalization layer includes sequentially fabricating one or more bilayers over the solid surface. Optionally, the outermost layer has a terminal azlactone moiety. In certain preferred embodiments, the one or more bilayers are fabricated using poly(2-vinyl-4,4'-dimethylazlactone) and branched poly(ethylene imine), and the outermost layer is fabricated using poly(2-vinyl-4,4'-dimethylazlactone).

The step of coating the solid surface with a chemical functionalization layer may additionally include the step of hydrolyzing the azlactone moieties of the outermost layer to carboxylic acid or carboxylate moieties. A preferred way to perform this step is by exposing the outermost layer to water vapor.

In a fourth aspect, the invention encompasses a method of using an immobilized liquid-based device to detect a target analyte. The method includes the steps of (a) providing an immobilized liquid-based device as described above, (b) contacting the device with a test sample, and (c) analyzing the immobilized liquid microdomains. In the method, a change in a measurable property of the liquid within the microdomains indicates the presence of the target analyte in the test sample.

In an alternative embodiment, the method includes the steps of (a) contacting one or more liquid microdomains having a minor axis of between about 0.5 μm and about 1000 μm with a test sample, (b) immobilizing the microdomains on a substrate surface by one or both of a covalent bond or a non-covalent attraction between a multifunctional polymer incorporated into the liquid microdomains and the substrate surface, and (c) analyzing the immobilized liquid microdomains. The multifunctional polymer may be incorporated into the liquid microdomains before, after, or at the same time as the contact between the microdomains and the test sample. As in the previously described embodiment, a change in a measurable property of the liquid within the microdomains indicates the presence of the target analyte in the test sample.

Preferably, the immobilized liquid microdomains used in the method are comprised of liquid crystal, and the change in the measurable property of the liquid within the microdomains is a change in the orientational order or phase of the liquid crystal microdomains. Such a change would include without limitation a transition from liquid crystal to isotropic liquid, as well as any change in anchoring configuration.

In a fifth aspect, the invention encompasses a method for spatially or temporally controlling the release or production of an active compound of interest. In some embodiments, the method includes the steps of (a) providing one or more liquid microdomains comprising a multifunctional polymer and one or more compounds of interest or one or more compounds that are capable of reacting to form a compound of interest, wherein the microdomains have a minor axis of between about 0.5 μm and about 1000 μm, (b) immobilizing the liquid microdomains onto a substrate surface by one or both of a covalent bond or a non-covalent attraction between the multifunctional polymer and the substrate surface, and (c) disrupting the liquid microdomains to release the contents of the liquid microdomains to the surrounding environment.

In a sixth aspect, the invention encompasses a method for "layer-by-layer" fabrication of a composite material at an interface. In some embodiments, the method includes the steps of (a) providing one or more liquid microdomains coated with a multifunctional polymer, wherein the microdomains have a minor axis of between about 0.5 μm and about 1000 μm, (b) immobilizing the liquid microdomains onto a substrate surface by one or both of a covalent bond or a non-covalent attraction between the multifunctional polymer and the substrate surface, and (c) sequentially repeating steps (a) and (b), wherein a multilayer-structure is formed at an interface.

Other objects, features and advantages of the present invention will become apparent after review of the specification, claims and drawings.

BRIEF DESCRIPTION OF THE DRAWINGS

FIG. 3: Schematic illustrations representing multilayered films A) presenting azlactone functionality (surface 1), G) terminated with a layer of BPEI (surface 2) and, J) treated to hydrolyze the azlactone functionality (surface 3). Polymer 1-coated LC droplets were dispersed onto the surface of these multilayered films: (B-D) surface 1, (H, I) surface 2, and (K-M) surface 3. Images in E and F were collected using uncoated LC droplets placed on surface 1. The droplets were given time to sediment to the surface of these films (B, E, H, and K) and then rinsed with fresh buffer (C, F, I, L, see text). In an additional step, droplets were rinsed with buffer containing 1.5 M NaCl (D, M). Scale bar=15 μm.

FIGS. 5: (A, B, E, F) Bright-field and (C, D, G, H) polarized light micrographs of polymer 1-laden 5CB droplets immobilized on (A-D) surface 1 and (E-H) surface 3. The images were captured with the focal plane of the microscope positioned at the middle of the droplets (A, C, E, G) or positioned at the apex of the droplets (B, D, F, H; see text). Scale bar=3 μm.

DETAILED DESCRIPTION OF THE INVENTION

I. In General

Figure 1:
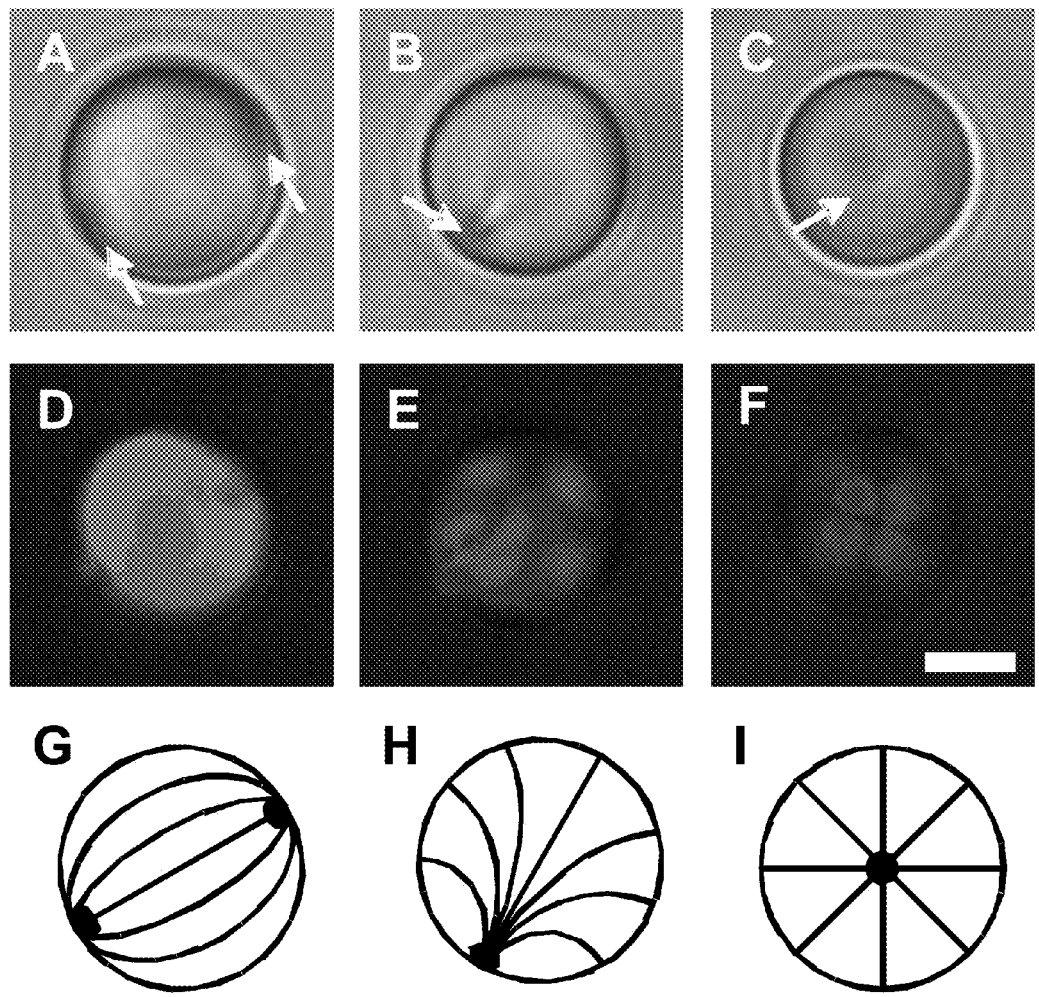
FIGS. 1: A-C) Bright-field and D-F) polarized light micrographs of dispersed 5CB droplets incubated in A, D) a buffer solution (10 mM HEPES, pH 7); B, E) a solution of polymer 1 at 0.1 mg/mL; and C, F) a solution of polymer 1 at 1.0 mg/mL. The 5CB emulsions were under continuous agitation for 2 h. G-I) Schematic illustrations of the director profiles for G) bipolar, H) preradial, and I) radial configurations. Point defects in the 5CB droplets shown in bright-field images are indicated by the white arrows. Scale bar=3 μm.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, "liquid crystal" means an organic composition in an intermediate or mesomorphic state between solid and liquid. Suitable liquid crystals for use in the present invention include, but are not limited to, thermotropic, polymeric, lyotropic, chromonic, smectic, nematic, ferroelectric and cholesteric liquid crystals.

A liquid "microdomain" refers to a volume of material in the liquid phase defined by an interface wherein the volume has a minor axis that is not at any point larger than 1000 μm across and wherein the minor axis is defined as the shortest length across the volume of the liquid microdomain. In the invention, liquid microdomains may be made up of liquid crystal or an isotropic oil.

A "multifunctional polymer" as used herein is a polymer having a structure that is capable of (a) adsorbing onto the interface of the liquid microdomains, and (b) facilitating the immobilization of the liquid microdomain onto the substrate surface.

The term "alkyl" as used herein refers to saturated, straight- or branched chain hydrocarbon radicals derived from a hydrocarbon moiety containing between one and twenty carbon atoms by removal of a single hydrogen atom. In some embodiments, alkyl groups have from 1 to 12, from 1 to 8 carbon atoms, from 1 to 6 or 1 to 3 carbon atoms. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl. A "cycloalkyl" group is a cyclic alkyl group typically containing from 3 to 8 ring members such as, but not limited to, a cyclopropyl, cyclobutyl, cyclopentyl, cyclohexyl, cycloheptyl, or cyclooctyl group.

The term "alkoxy" as used herein refers to an alkyl group, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy groups.

The term "alkenyl" denotes a monovalent group derived from a hydrocarbon moiety having at least one carbon-carbon double bond by the removal of a single hydrogen atom. Alkenyl groups include, for example, ethenyl, propenyl, butenyl, I-methyl-2-buten-1-yl, and the like. Alkenyl groups include those having from 2-12 carbon atoms, those having 2-8, and those having 2-6 carbon atoms.

The term "alkynyl" as used herein refers to a monovalent group derived from a hydrocarbon having at least one carbon-carbon triple bond by the removal of a single hydrogen atom. Representative alkynyl groups include ethynyl, 2-propynyl (propargyl), I-propynyl, and the like. Alkynyl groups include those having from 2-12 carbon atoms, those having 2-8, and those having 2-6 carbon atoms.

The term "aryl" as used herein refers to carbocyclic ring systems having at least one aromatic ring including, but not limited to, phenyl, naphthyl, tetrahydronaphthyl, indanyl, and indenyl groups, and the like. Aryl groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. In addition, substituted aryl groups include tetrafluorophenyl and pentafluorophenyl.

The term "alkylene" refers to a diradical of a branched or unbranched saturated hydrocarbon chain, preferably having from 1 to 10 carbon atoms, including 1-6 carbon atoms, and 2-4 carbon atoms. This term is exemplified by groups such as methylene (—CH2-), ethylene (—CH2CH2-), more generally —(CH2)n, where n is and integer from 1-about 20, including 1-10, 1-6 or 2, 3 or 4. Alkylene groups may be branched. Alkylene groups may be optionally substituted. Alkylene groups may have up to two non-hydrogen substituents per carbon atom. which do not interfere with removal of removable functional groups.

The term "alkyleneoxy" refers to an alkylene group ads described above in which one or more non-neighboring —CH—, —CH2- or substituted —C— are replaced with an oxygen atoms, e.g., —CH2-CH2-O—CH2-CH2-, —O—CH2-CH2-, —CHCH3-OCH2-CH2-. The alkyleneoxy group can be branched or unbranched. The carbons of alkyleneoxy groups are optionally substituted with non-hydrogen substituents which do not interfere with removal of removable functional groups.

The term "carbocyclic" is used generally herein to refer to groups containing one or more carbon rings. The groups may be aromatic or aryl groups. Rings may contain 3-10 carbon atoms and one, two or three double bonds or a triple bond. These groups may include single rings of 3 to 8 atoms in size and bi- and tri-cyclic ring systems which may include aromatic six-membered aryl or aromatic groups fused to a non-aromatic ring.

The terms "heterocyclic" and "heterocyclyl", are used broadly herein to refer to an aromatic, partially unsaturated or fully saturated 3- to 10-membered ring system, which includes single rings of 3 to 8 atoms in size and bi- and tricyclic ring systems which may include aromatic six-membered aryl or aromatic heterocyclic groups fused to a non-aromatic ring. These heterocyclic and heterocyclyl rings and groups include those having from one to three heteroatoms independently selected from oxygen, sulfur, and nitrogen, in which the nitrogen and sulfur heteroatoms may optionally be oxidized and the nitrogen heteroatom may optionally be quaternary.

The terms "aromatic heterocyclic" or "heteroaryl" as used herein, refer to a cyclic aromatic radical having from five to 12 ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms. The term includes heteroaromatic rings fused to aryl ring or to carbocylci rings. Examples of such aromatic heterocyclyl groups include, but are not limited to, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl groups, and the like.

The term "hydrocarbon", as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include without limitation methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms "substituted", whether preceded by the term "optionally" or not, and "substituent", as used herein, refer to the ability, as appreciated by one skilled in this art, to change one functional group for another functional group, provided that the valency of all atoms is maintained. When more than one position in any given structure may be substituted with more than one substituent selected from a specified group, the substituent may be either the same or different at every position. The substituents may also be further substituted (e.g., an aryl group substituent may be further substituted). A non limiting example is an aryl group that may be further substituted with, for example, a fluorine group at one or more position.

The following abbreviations are used throughout the present disclosure: LC, liquid crystal; 5CB, 4'-pentyl-4-cyanobiphenyl; LPEI, linear poly(ethylene imine); HEPES, 4-(2-Hydroxyethyl-1-piperazineethanesulfonic acid); FITC-dextran, fluorescein isothiocyanate labeled dextran; VDMA, 2-Vinyl-4,4-dimethylazlactone; PVDMA, poly(VDMA); TMR-NHS, carboxytetramethylrhodamine succinimidyl ester; PM-IRRAS, polarization-modulation infrared reflectance-absorbance spectroscopy; LSCM, laser scanning confocal microscopy; DMSO, dimethyl sulfoxide; BPEI, branched poly(ethylene imine).

II. The Invention

The inventors have discovered that the assembly of multifunctional polymers on the interfaces of micrometer-sized droplets of a thermotropic liquid crystal (LC) dispersed in aqueous solutions can be used to facilitate the immobilization of LC droplets on chemically functionalized surfaces. The assembly of the multifunctional polymer at the interfaces of the aqueous dispersions of LC droplets was achieved by spontaneous adsorption of polymer from the surrounding aqueous solution. Polymer adsorption triggered transitions in the orientational ordering of the LCs, as observed by polarized light and bright-field microscopy.

The presence of the polymer on the interfaces of these droplets can be exploited to immobilize LC droplets on planar solid surfaces through covalent bond formation or through non-covalent interactions, including but not limited to electrostatic interactions. Characterization of immobilized LC droplets by polarized, fluorescence, and laser scanning confocal microscopy revealed the general spherical shape of the polymer-coated LC droplets to be maintained after immobilization, and that immobilization led to additional ordering transitions within the droplets that were dependent on the nature of the surfaces with which they were in contact.

Polymer functionalized LC droplets were not immobilized on polymer multilayers treated with poly(ethylene imine) (PEI), demonstrating that the ability to design surfaces that promote or prevent the immobilization of polymer-functionalized LC droplets can exploited to pattern the immobilization of LC droplets on surfaces. These results provide the basis of an approach that could be used to tailor the properties of dispersed LC emulsions and to immobilize these droplets on functional surfaces of interest in a broad range of fundamental and applied contexts.

Accordingly, the present invention provides devices having liquid microdomains immobilized on a substrate surface, methods of making and using such devices, and methods of immobilizing liquid microdomains on a surface substrate. In this patent application we define the term liquid droplet to be a liquid microdomain, but the liquid microdomains of the invention are not limited to only liquid droplets or to droplets dispersed in aqueous solutions. In addition, the shape of the domain is not limited to a spherical shape. Shapes other than spherical, including hemispherical shapes formed by droplets on surfaces, are covered within the scope of this invention.

It should also be recognized by those skilled in the art that the devices and methods described in this invention are not limited to using LC as the liquid making up the liquid microdomains. Isotropic liquids, including without limitation oil droplets, can also be immobilized by the methods reported herein.

As one skilled in the art would recognize, the device and methods of the present invention would have many uses, including without limitation for detecting and measuring analytes in a sample and for the fabrication of liquid crystal-based devices such as devices engineered to possess optical band gaps. In particular, organized arrays of LC microdomains can define optical band-gap materials and the scope of the invention includes use of such collective optical behaviors exhibited by arrays of immobilized LC microdomains.

The feasibility of the approach has been established in the following example. In the example, the liquid crystal used is 4-cyano-4'-pentylbipheny-1 (5 CB). These molecules can be assembled into a so-called nematic LC phase, where the molecules exhibit long-range orientational order that is not found in isotropic liquids. As LCs are essentially ordered oils, emulsions containing droplets of nematic phase LC dispersed in aqueous phases can be created, or domains of LC can be contacted with aqueous phases without dissolution of the LC into the aqueous phase. A large number of methods can be used to create the LC microdomains, including sonication of LC in an aqueous phase, extrusion through a membrane, mechanical agitation, flow focusing, including flow focusing in microfluidic channels. Similar methods can be used to create microdomains using isotropic liquids, such as oils, for use in the invention.

In a first aspect, the invention encompasses an immobilized liquid-based device having one or more liquid microdomains immobilized on a substrate surface. The preferred size for the liquid microdomains of the present invention is a minor axis of between about 0.5 µm and about 1000 µm, with a more preferred size being a minor axis of between about 0.5 µm and about 200 µm, and a most preferred size being a minor axis between about 0.5 µm and about 10 µm.

A variety of liquids may be used in making the liquid microdomains of the present invention, including without limitation various isotropic oils and liquid crystals. Examples of suitable liquid crystals, include, but are not limited to, 4-cyano-4'-pentylbiphenyl (5 CB), 7 CB, and 8 CB, and E7 and TL205. A large listing of suitable liquid crystals is presented in "Handbook of Liquid Crystal Research" by Peter J. Collings and Jay S. Patel, Oxford University Press, 1997, ISBN 0-19-508442-X. Polymeric liquid crystals are also suitable for use in the device and methods of the present invention. Because the devices and methods of the present invention may be used to contact the liquid microdomains with aqueous test solutions, preferred liquid crystals and isotropic oils employed in the invention would be insoluble in water or have very limited solubility in water. Additionally, preferred liquid crystals and isotropic oils employed in the invention would not react with water.

In certain embodiments of the present invention, the liquid crystal comprising the microdomains is 4-cyano-4'-pentylbipheny-1 (5 CB). Although various types of liquid crystal or isotropic oils may be employed, nematic and thermotropic liquid crystals are preferred. However, smectic liquid crystals formed from 8 CB are also suitable for use in the present invention. Suitable liquid crystals further include smectic C, smectic C*, blue phases, cholesteric phases, smectic A, and polymeric liquid crystals.

In certain preferred embodiments, the liquid microdomains are dispersed as an emulsion of liquid droplets within another liquid and subsequently immobilized onto the substrate surface. In such embodiments, the liquid microdomains are preferably dispersed within an aqueous solution. The aqueous solution may be buffer free, or may be a buffer solution. Although a variety of standard buffer solutions would be suitable, preferred buffer solutions for use in the invention include phosphate buffered saline (PBS) and HEPES buffer.

As one skilled in the art would recognize, the liquid droplet-aqueous emulsions can be made in a number of ways. Preferably, the emulsion is made by sonicating and vortexing a mixture containing liquid crystal or isotropic oil and a buffer, and more preferably, the sonication and vortexing process are alternated a number of times, most preferably through twelve or more cycles of sonicating and vortexing. In other embodiments, the emulsions are made using microfluidic channels with flow focusing, or made by passing the liquid crystal or isotropic oil and aqueous solution through an orifice or orifices.

The immobilized liquid microdomains that are part of the device have a multifunctional polymer adsorbed on the microdomain surface. A "multifunctional polymer" as used herein is a polymer having a given structure that is capable of (a) adsorbing onto the interface of the liquid microdomains, and (b) facilitating the immobilization of the liquid microdomain onto the substrate surface.

In certain preferred embodiments, the multifunctional polymer possesses chemical functional groups that enable the immobilization of the liquid microdomains to the substrate surface through covalent or non-covalent interactions. In addition, the multifunctional polymer has a structure such that it can be readily adsorbed onto the surface of the liquid microdomain interface. Such multifunctional polymers are not limited to amphiphilic polymers, as used in the example below. For example, because the zeta potentials of LC droplets dispersed in water are typically non-zero, and thus non-amphiphilic, charged polymers will also adsorb onto LC droplets. It is also well known by those skilled in the art that neutral polymers such as polyvinylalcohol (PVA) will adsorb on the aqueous-LC interface. Thus a "multifunctional polymer" is not limited by the presence or absence of specific single or multiple functional groups.

As a non-limiting example, a multifunctional polymer may be a polymer having the structure comprised of repeats of units X and Y, where X is a class of repeat units present to promote adsorption onto the interface of the liquid microdomains, and Y is a class of repeat units present to promote the immobilization of the liquid microdomain onto the substrate surface. The term "multifunctional polymer" includes polymers that contain only one functionality that performs both the X and Y function. In such embodiments, X and Y may have the same structure, resulting in a polymer that may be recognized in the art as "unifunctional." Such polymers would be considered "multifunctional polymers" as the term is used herein and in the claims, because the same functionality would both promote adsorption onto the interface of the liquid microdomain and the immobilization of the liquid microdomain onto the substrate surface. We also emphasize that X may comprise a plurality of functional groups that serve to promote adsorption to the liquid microdomains, and that Y may also comprise a plurality of functional groups that serve to promote immobilization of liquid microdomains.

Examples of X include without limitation repeat units in the polymer with hydrophobic side chains, such as aliphatic, cyclic hydrophobic, branched aliphatic, or aromatic groups, including without limitation alkyl, cycloalkyl, alkoxy, alkenyl, alkynyl, alkylene, alkyleneoxy, aryl, carbocyclic, heterocyclic, and heteroaryl groups, including substituted alternatives thereof. Guidance as to the scope of the functional groups that comprise X can be obtained from prior art that describes the design of molecules with hydrophobic domains that promote adsorption of molecules at aqueous interfaces, this includes such groups as oligopropyleneoxide and polystyrene. The functional groups X can also be selected from all classes of naturally occurring and semi-synthetic groups, such as amino acids, lipids, fats glycolipids and sugars. It also includes substantially apolar functional groups.

Y incorporates without limitation all functional groups described in Greg T. Hermanson, Bioconjugate Techniques (Academic Press, 1996), which is incorporated by reference herein in its entirety. Examples of Y include without limitation a charged or chemically reactive group, including azlactone, alkynes, azides, NHS-activated acids, amine groups, aldehydes, light-activatable cross-linkers, thiols, hydroxyl groups, and activated esters, such as (but not limited to) pentafluorophenyl esters. Y additionally includes other chemically reactive groups widely used in conjugation chemistry.

There are a number of ways the multifunctional polymer can be incorporated into the liquid microdomains, but preferably, the polymer is water soluble, and is adsorbed at the interface between the liquid microdomains from a surrounding aqueous solution. An alternative approach which falls within the scope of the invention is to dissolve the polymer within the liquid making up the microdomains (such as an LC or oil), and to let it adsorb to the interface from the liquid.

A wide range of multifunctional polymers can be used to make the devices and to practice the methods of the present invention. In some embodiments, the polymer is an amphiphilic polymer. In some such embodiments, the amphiphilic polymer is a polyamine. Such polyamines may incorporate side chains having primary amines, to facilitate the immobilizing attraction to the substrate surface. Side chains having tertiary amines may also be incorporated into the amphiphilic polymer, to further enhance the hydrophilic functionality of the polymer. The hydrophobic functionality of the amphiphilic polymer may be enhanced by the incorporation of one or more long aliphatic side chains into the amphiphilic polymer. A non-limiting example of such a side chain is a side chain terminating in an alkyl moiety of at least five carbons in length. A preferred amphiphillic multifunctional polymer, designated polymer 1, is represented by the following chemical structure:

Polymer 1

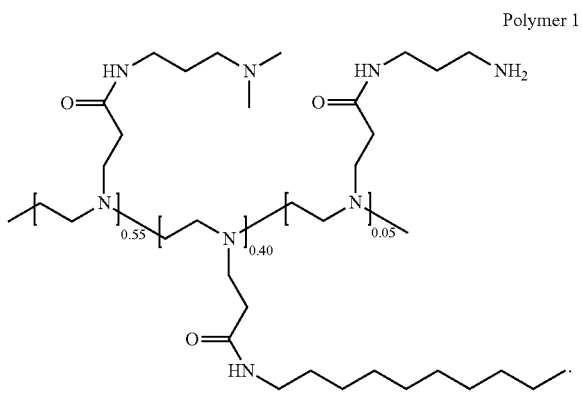

The device also includes a substrate surface on which the liquid microdomains are immobilized. The immobilization of the microdomains on the substrate surface is the result of one or more attractions between the multifunctional polymer and the substrate surface. The attraction immobilizing the liquid microdomain can be a covalent bond or a non-covalent bond. Examples of non-covalent bonds that could be used to immobilize the liquid microdomains on the substrate surface include without limitation electrostatic attractions, hydrophobic interactions, dative interactions, coordination bonds, metal-mediated interactions, or other interaction between the multifunctional polymer and the substrate surface.

The substrate surface can be made of any material that facilitates attraction between the amphiphillic polymer incorporated into the LC microdomains and the surface. Preferably, the substrate surface is a solid surface coated with a chemical functionalization layer on which one or more of the microdomains is immobilized. Many types of functional surfaces can be used, including without limitation functionalized self-assembled monolayers (SAMs), surfaces of glass or other materials having covalent modifications to render them reactive/interactive, or functional polymers adsorbed onto surfaces using conventional methods not related to the fabrication of multilayers, such as simple adsorption of a polymer to a surface. In certain embodiments, the chemical functionalization layer is a chemically functionalized polymer multilayer, such as a multilayer film that is deposited on the solid surface through layer by layer deposition methods that are known in the art.

A number of different terminal chemical moieties could be used to chemically functionalize the outer layer of the polymer multilayer, including the moieties listed above as examples of the Y unit of the multifunctional polymer. Y incorporates all functional groups described in Greg T. Hermanson, Bioconjugate Techniques (Academic Press, 1996), which is incorporated by reference herein in its entirety. Examples of Y include without limitation a charged or chemically reactive group, including azlactone, alkynes, azides, NHS-activated acids, amine groups, aldehydes, light-activatable cross-linkers and chemically reactive groups widely used in conjugation chemistry.

In certain embodiments, the outer layer of the polymer multilayer is functionalized with one or more of terminal azlactone moieties, terminal carboxylic acid moieties, or terminal carboxylate moieties. Azlactone moieties facilitate covalent bonding of the polymer multilayer with the multifunctional polymer, while both carboxylic acid and carboxylate moieties facilitate electrostatic attraction between the polymer multilayer and the multifunctional polymer.

In certain preferred embodiments, chemically functionalized polymer multilayer is composed of one or more bilayers that are sequentially deposited onto the substrate surface. In a non-limiting example of such an embodiment, bilayers may be composed of alternating layers of branched poly(ethylene imine) (BPEI) and poly(2-vinyl-4,4'-dimethylazlactone) (PVDMA). In this specific bilayer example, the multilayer is terminated by a final outer layer of PVDMA, providing the preferred azlactone functionality. Alternatively, the terminal azlactone moieties on the outer PVDMA layer are hydrolyzed by exposure to saturated water vapor or by other methods known in the art to provide the preferred carboxylic acid or carboxylate functionality.

The outer layer of the polymer multilayer on the surface substrate may be fabricated to cover all of the substrate surface, or the outer layer may be limited to covering only specific portions of the substrate surface. Thus, the preferred functionality of the outer layer of the substrate surface polymer multilayer can be patterned or spatially defined to provide further control over the immobilization of the LC microdomains. In a non-limiting example of such surface patterning, the BPEI/PVDMA polymer multilayer discussed in the previous paragraph is terminated by an outer layer of BPEI, rather than a layer of PVDMA. The BPEI outer layer does not have the preferred functionality, and so does not facilitate LC microdomain immobilization. However, by selectively delivering PVDMA solution onto the outer BPEI layer only where such functionality is desired, a spatially customized outer PVDMA layer containing the preferred functionality can be assembled on the substrate surface.

In a second aspect, the invention encompasses a method of immobilizing liquid crystal microdomains on a substrate surface. The method includes the step of coating a solid surface with a chemical functionalization layer to form a substrate surface. The preferred characteristics of the chemical functionalization layer have been reviewed previously. For example, in certain embodiments, the chemical functionalization layer is a polymer multilayer functionalized by one or more of a terminal azlactone moiety (to facilitate covalent bonding), a terminal carboxylic acid moiety (to facilitate electrostatic attraction), and a terminal carboxylate moiety (to facilitate electrostatic attraction).

A variety of methods known in the art can be used to coat the solid surface with a polymer multilayer having such properties. As a non-limiting example, one or more bilayers could be fabricated sequentially over the solid surface, with the final outer layer having a terminal azlactone moiety. Specifically, alternating layers of poly(2-vinyl-4,4'-dimethylazlactone) and branched poly(ethylene imine) could be sequentially deposited onto the substrate surface, terminating with a layer of poly(2-vinyl-4,4'-dimethylazlactone). The outer PVDMA layer would have the preferred azlactone functionality.

Alternatively, the azlactone moieties of the outermost layer of the polymer multilayer may be further hydrolyzed to carboxylic acid or carboxylate moieties. Hydrolysis may be performed using a variety of methods known in the art, including without limitation exposing the outermost layer of the multilayer polymer to water vapor, preferably saturated water vapor.

In some embodiments, the outermost layer of the polymer multilayer is fabricated to cover less than the entire substrate surface. In a non-limiting example of such surface patterning, a BPEI/PVDMA polymer multilayer may be terminated by an outer layer of BPEI, rather than a layer of PVDMA. Then, a spatially customized outer PVDMA layer containing the preferred functionality (i.e. azlactone) can be selectively deposited by delivering PVDMA solution onto the outer BPEI layer only where such functionality is desired.

Once the desired polymer multilayer has been coated onto the solid surface to form the substrate surface, one or more liquid microdomains having a minor axis of between about 0.5 µm and about 1000 µm and further incorporating a multifunctional polymer are contacted with the substrate surface, resulting in the immobilization of the microdomains on the substrate surface. The preferred characteristics of the microdomains and the multifunctional polymer, and preferred methods of incorporating the multifunctional polymer into the LC microdomains are further discussed above and illustrated in the example below.

In a third aspect, the invention encompasses a method of making an immobilized liquid microdomain-based device having liquid microdomains immobilized on a substrate surface. The method includes the steps of coating a solid surface with a chemical functionalization surface to form a substrate surface and contacting one or more liquid microdomains having a minor axis of between about 0.5 µm and about 1000 µm and further incorporating a multifunctional polymer with the substrate surface. The liquid crystal microdomains are subsequently immobilized on the substrate surface. These steps are discussed further above in connection with the claimed method of immobilizing liquid microdomains on a substrate surface and are further illustrated in the example below.

In a fourth aspect, the invention encompasses a method of using an immobilized liquid microdomain-based device having liquid microdomains immobilized on a substrate surface for analyte detection. This method includes the steps of providing an immobilized liquid microdomain-based device as described above and illustrated in the example below, contacting the device with an test sample, and analyzing the immobilized liquid crystal microdomains to determine the presence of the target analyte in the test sample. In an alternative embodiment, the liquid microdomains used to make the device may be contacted with the test sample before the liquid microdomains are immobilized on a substrate to make the device. Preferably, the microdomains are comprised of liquid crystal. A variety of methods known in the art may be used to analyze the immobilized liquid microdomains, including without limitation using a detector to detect the anchoring configuration of the liquid crystal microdomains.

Within droplets of LC, the organization of the LC, known as the "anchoring configuration," depends strongly on the state of the interface between the LC and aqueous phase. Depending on the size of the droplets and the structure, concentration and organization of any interfacial adsorbates, the anchoring configuration of the LC within the droplets can vary substantially, and this variation can be detected using optical and other detection methods. See Gupta et al. Angew. Chem. Int. Ed. 2008, 48, 1652-55. The configuration of the LC is dictated by the interfacial interactions of the LC as well as the energy stored in the volume of the LC droplets as a consequence of elastic strain of the LC.

FIGS. 1A and 1D show representative bright-field and polarized light micrographs, respectively, of LC droplets in HEPES buffer (i.e., in the absence of polymer). These LC droplets exhibit a so-called bipolar configuration in which the director of the LC is oriented parallel to the surface of the droplets and connects two point defects located at opposite poles of the droplet. FIG. 1G presents a schematic illustration of this director profile. These point defects scatter light, and can thus be observed by bright-field microscopy (e.g., indicated by the white arrows in FIG. 1A).

The inventors observed large changes in the ordering of LC within droplets incubated in the presence of a multifunctional polymer. These changes are exemplified by the bright-field and polarized light micrographs shown in FIGS. 1B, 1C, 1E, and 1F. The images in FIGS. 1B and 1E correspond to droplets incubated in a solution of polymer. In contrast to the images shown in FIGS. 1A and 1D, these images reveal the presence of a single point defect located at the surface of the droplet (e.g., indicated by the white arrow in FIG. 1B). The presence of this single point defect is consistent with a shift of the orientation of the LC from a bipolar configuration to a so-called preradial configuration, in which the director radiates outward from the single point defect (see FIG. 1H for a schematic illustration).

Because the director profile for the preradial configuration is not spherically symmetric (that is, the point defect is not located in the center of the sphere), the apparent location of the defect changes as the droplet rotates in solution. This characteristic allows this type of defect to be identified easily and distinguished from the so-called radial configuration in which the defect is located in the geometric center of the LC droplet (and, thus, does not move as the droplet rotates; see FIG. 1I for a schematic illustration of this configuration). The inventors observed radial configurations in bright-field images of LC droplets incubated in the presence of higher concentrations of multifunctional polymer as shown in FIG. 1C. This radial configuration leads to a characteristic cross-like pattern when viewed under polarized light (FIG. 1F).

In certain embodiments, the device is contacted with an aqueous solution potentially containing an analyte of interest, and the analyte is detected within the aqueous solution by contact with the immobilized LC microdomains. On contact with the analyte of interest, the immobilized LC microdomains may change their anchoring configuration. Thus, preferably, a detector capable of detecting and reporting the anchoring configuration of the liquid crystal droplets may be used in conjunction with the device. Because anchoring configuration of liquid crystal droplets can be determined using either polarized microscopy or bright field microscopy, an optical microscope can be used as the detector in certain embodiments of the method.

More generally, the scope of the method of using the device includes the use of polarized light or non-polarized light to detect the configuration of the LC within the immobilized microdomains. Because defects formed within the LC droplets scatter light, it is also possible to detect the configuration of LC within the LC microdomains by measurement of the scattering of non-polarized light. The light can be monochromatic, white light, or colored light comprising a mixture of wavelengths, and all can be employed in the practice of this invention.

The step of using a detector to detect and report any change in configuration of the liquid crystal droplets can be performed by a number of different methods known in the art, including without limitation polarized microscopy, interaction of polarized light with the LC droplets, light scattering, bright field microscopy, optical microscopy, fluorescence microscopy, fluorescence spectrophotometry, turbidity, optical transmission measurements, visual inspection, flow cytometry, microfluidic chips with optical detection systems integrated within, fluorescence flow cytometry, or microelectrophoresis, electrophoresis and dielectrophoresis.

In a fifth aspect, the invention encompasses a method for spatially or temporally controlling the release or production of an active compound of interest. The active compound of interest could be any compound having a particular desired property. Non-limiting examples of such compounds of interest include drugs and pharmaceuticals, antimicrobial compounds, adhesives, fragrances, and luminescent materials.

In some embodiments, the method includes the steps of (a) providing one or more liquid microdomains comprising a multifunctional polymer and one or more compounds of interest or one or more compounds that are capable of reacting to form a compound of interest, wherein the microdomains have a minor axis of between about 0.5 µm and about 1000 µm, (b) immobilizing the liquid microdomains onto a substrate surface by one or both of a covalent bond or a non-covalent attraction between the multifunctional polymer and the substrate surface, and (c) disrupting the liquid microdomains to release the contents of the liquid microdomains to the surrounding environment. In yet other embodiments, the method includes the steps of (a) providing one or more liquid microdomains comprising a multifunctional polymer, wherein the microdomains have a minor axis of between about 0.5 µm and about 1000 µm, (b) immobilizing the liquid microdomains onto a substrate surface by one or both of a covalent bond or a non-covalent attraction between the multifunctional polymer and the substrate surface, (c) incorporating one or more compounds of interest or one or more compounds that are capable of reacting to form a compound of interest into the immobilized liquid microdomains, and (d) disrupting the liquid microdomains to release the contents of the liquid microdomains to the surrounding environment.

The liquid used in the liquid microdomains is preferably an oil or a liquid crystal. The compounds included in the microdomains may be the liquid of the liquid microdomain, or may be a separate compound dissolved within the liquid of the liquid microdomains. In certain embodiments, different liquid microdomains include different compounds. For example, in some such embodiments, two different compounds, compound A and compound B, may react together to produce the compound of interest. Compound A and Compound B may be incorporated into two separate types of liquid microdomain, either as the liquid itself or as a further component dissolved within the liquid. Upon disruption and release of the contents of the microdomains, the subsequent mixing of compound A and compound B would lead to the production of the compound of interest. In other embodiments, the compound of interest is incorporated directly into the liquid microdomains, either as the liquid itself or dissolved within the liquid. Upon disruption and release of the liquid microdomains, the compound of interest is released directly into the surrounding environment. Disruption of the liquid microdomains can be performed by a number of techniques known in the art, including without limitation mechanical and chemical disruption.

In a sixth aspect, the invention encompasses a method for "layer-by-layer" fabrication of a composite material at an interface. In some embodiments, the method includes the steps of (a) providing one or more liquid microdomains coated with a multifunctional polymer, wherein the microdomains have a minor axis of between about 0.5 µm and about 1000 µm, (b) immobilizing the liquid microdomains onto a substrate surface by one or both of a covalent bond or a non-covalent attraction between the multifunctional polymer and the substrate surface, and (c) sequentially repeating steps (a) and (b), wherein a multilayer-structure is formed at an interface. In yet other embodiments, the method includes the steps of (a) providing one or more liquid microdomains comprising a multifunctional polymer, wherein the microdomains have a minor axis of between about 0.5 µm and about 1000 µm, (b) immobilizing the liquid microdomains onto a substrate surface by one or both of a covalent bond or a non-covalent attraction between the multifunctional polymer and the substrate surface, (c) adsorbing or reacting a polymer on the substrate surface, and sequentially repeating steps (a)-(c), wherein a wherein a multilayer-structure is formed at an interface. A structure produced by the method could serve as a photonic crystal or be used in a manner similar to that described in connection with the fifth aspect of the invention, further discussed above.

The following example is offered for illustrative purposes only, and is not intended to limit the scope of the present invention in any way. Indeed, various modifications of the invention in addition to those shown and described herein will become apparent to those skilled in the art from the foregoing description and the following examples and fall within the scope of the appended claims.

III. Example

Immobilization of Polymer-Decorated Liquid Crystal Droplets on Chemically Tailored Surfaces Introduction.

The following Example is organized into three parts. First, the inventors describe the design of an amphiphilic polymer containing primary, secondary, and tertiary amine functionality, and demonstrate that this polymer can adsorb to the interfaces of micrometer-scale droplets of 5CB in aqueous/LC emulsions. Evidence of adsorption is provided by the observation of changes in the ordering and defect structures of the LCs and by the results of experiments using fluorescently labeled polymer.

In the second part, the inventors investigate the nature of interactions between polymer-decorated LC droplets and surfaces coated with several different chemically functionalized polymer multilayers. The results demonstrate that polymer-functionalized droplets can be effectively immobilized on these surfaces. In the case of surfaces presenting amine-reactive azlactone functionality, the results suggest that immobilization occurs through the formation of covalent bonds between accessible primary amines on the interfaces of the polymer-coated droplets and the azlactone functionality at the surface of the substrates. In the case of carboxylic-acid presenting surfaces, the results suggest that these polymer-coated droplets can also be immobilized through electrostatic interactions. Characterization of individual immobilized droplets by polarized light microscopy reveals that contact with these surfaces leads to distinct changes in the ordering of the LC that are dependent on the physicochemical properties of the surfaces.

In the final part of this Example, the inventors demonstrate that it is possible to spatially pattern polymer-functionalized droplets of LC on the surfaces of chemically patterned substrates. The results suggest approaches to manipulate and characterize the behavior of dispersed polymer-functionalized LC droplets of interest in a range of fundamental and applied contexts.

Materials and Methods.

Materials.

Linear poly(ethylene imine) (LPEI) was synthesized by hydrolysis of the side chains of poly(2-ethyloxazoline) [MW=50,000; obtained from Polysciences, Inc., Warington, Pa.] and purified prior to use in analogy to procedures described previously (Tanaka, R.; Ueoka, I.; Takaki, Y.; Kataoka, K.; Saito, S. Macromolecules 1983, 16, 849). 4-(2-Hydroxyethyl-1-piperazineethanesulfonic acid) (HEPES), sodium chloride, methanol, ethanol, dimethyl sulfoxide (DMSO), ethyl acetate, chloroform, dichloromethane, hexanes, trifluoroacetic acid, and glass cover slips were purchased from Fisher Scientific (Pittsburgh, Pa.). Acryloyl chloride, n-decylamine, 3-(dimethylamino)-1-propylamine, 1,3-diaminopropane, di-tert-butyl dicarbonate, branched poly(ethylene imine) [BPEI, MW=25,000], fluorescein isothiocyanate labeled dextran [FITC-dextran, MW=2,000,000], and 2,2'-azobisisobutyronitrile were purchased from Sigma-Aldrich (St. Louis, Mo.). 2-Vinyl-4,4-dimethylazlactone (VDMA) was a generous gift from Dr. Steven Heilmann (3M Corporation, St. Paul, Minn.). N-Decylacrylamide, N-[3-(dimethylamino)propyl]acrylamide, N-[3-(tert-butoxycarbonylamino)propyl]acrylamide, and poly(VDMA) (PVDMA) were synthesized in analogy to previously described procedures (Guichard, B.; Noel, C.; Reyx, D.; Thomas, M.; Chevalier, S.; Senet, J. P. Macromol. Chem. Phys. 1998, 199, 1657; Kuroda, K.; DeGrado, W. F. J. Am. Chem. Soc. 2005, 127, 4128; Liu, X. H.; Yang, J. W.; Miller, A. D.; Nack, E. A.; Lynn, D. M. Macromolecules 2005, 38, 7907).

Carboxytetramethylrhodamine succinimidyl ester (TMR-NHS) was purchased from Molecular Probes (Carlsbad, Calif.). The LC 4-cyano-4'-pentylbiphenyl (5CB) was obtained from EMD Chemicals (Hawthorne, N.Y.). Glass beads (diameter=3-10 μm) were purchased from Polysciences, Inc. Deionization of a distilled water source was performed using a Milli-Q system (Millipore, Bedford, Mass.) yielding water with a resistivity of 18.2 MΩ. All materials were used as received and without additional purification unless otherwise noted.

General Considerations.

Nuclear magnetic resonance (NMR) spectra were recorded on a Bruker AC+300 spectrometer (300.135 MHz for proton; Billerica, Mass.). Chemical shift values are given in ppm and are referenced with respect to residual protons from solvent. Polarized light, bright-field, and fluorescence microscopy images of 5CB droplets were acquired using an Olympus IX-71 inverted microscope equipped with a 100 W mercury lamp and filter cube with a 560 nm excitation filter and a 645 nm emission filter. Images were captured using a Hamamatsu 1394 ORCA-ER-CCD camera controlled with SimplePCI software (Hamamatsu Inc., Sewickly, Pa.). Laser scanning confocal microscopy (LSCM) was performed using a Bio-Rad Radiance 2100 MP Rainbow laser scanning confocal microscope. Tetramethylrhodamine and fluorescein were excited sequentially using laser lines at 543 nm and 488 nm, respectively, and fluorescence emission was collected individually from the red and green channels. Silicon substrates used for reflective infared spectroscopy experiments were prepared by depositing thin layers of titanium (10 nm) and gold (200 nm) sequentially onto silicon wafers (Si-Tech, Inc., Topsfield, Mass.) using an electron-beam evaporator (Tek-Vac Industries, Brentwood, N.Y.). Characterization of multi-layered films by polarization-modulation infrared reflectance-absorbance spectroscopy (PM-IRRAS) was conducted in analogy to previously reported methods (Buck, M. E.; Zhang, J.; Lynn, D. M. Adv. Mater. 2007, 19, 3951). All experiments involving the use of 5CB were performed at ambient room temperature (~25° C.), well below the nematic/isotropic transition temperature of 5CB (33.5° C.) unless otherwise noted.

Synthesis of Polymer 1.

The synthesis of polymer 1 was performed by the conjugate addition of LPEI to acrylamide compounds in analogy to previously published methods (Kuroda, K.; DeGrado, W. F. J. Am. Chem. Soc. 2005, 127, 4128; Liu, X. H.; Yang, J. W.; Miller, A. D.; Nack, E. A.; Lynn, D. M. Macromolecules 2005, 38, 7907). N-[3-(tert-Butoxycarbonylamino)propyl] acrylamide (13.1 mg, 0.058 mmol) was added to a solution of LPEI (50 mg, 1.16 mmol) in methanol in a screw-capped vial equipped with a magnetic stir bar. The reaction solution was stirred at 50° C. for 7 days at which time N-decylacrylamide (98.2 mg, 0.46 mmol) was added. The reaction mixture was stirred for an additional 7 days at which time N-[3-(dimethylamino)propyl]acrylamide (218 mg, 1.39 mmol) was added and the reaction mixture was allowed to stir for an additional 7 days. The resulting reaction product was isolated by repeated precipitation into a mixture of hexanes and diethyl ether (9:1, v/v) to yield the Boc-protected polymer. Removal of the Boc protecting group was achieved by dissolving the polymer in a mixture of dichloromethane and trifluoroacetic acid (1:1, v/v) in a screw-capped vial equipped with a magnetic stir bar. The reaction mixture was stirred for two hours at room temperature.

The resulting reaction product was isolated by precipitation into a mixture of hexanes and diethyl ether (5:1, v/v) to yield polymer 1 as a tacky, viscous oil. $M_n$=29,500; PDI=3.7. $^1$H NMR (CDCl$_3$) δ (ppm) 0.877 (t, —NHCH$_2$CH$_2$(CH$_2$)$_7$CH$_3$), 1.17 (br, —NHCH$_2$CH$_2$(CH$_2$)$_7$CH$_3$), 1.38 (m, —NHCH$_2$CH$_2$(CH$_2$)$_7$CH$_3$), 1.80-1.85 (b, —NHCH$_2$CH$_2$CH$_2$N(CH$_3$)$_2$, —NHCH$_2$CH$_2$CH$_2$N$_2$), 2.81 (s, —NHCH$_2$CH$_2$CH$_2$N(CH$_3$)$_2$), 2.87-3.27 (br m), 3.36-3.42 (b, m, —NHCH$_2$CH$_2$(CH$_2$)$_7$CH$_3$, —NHCH$_2$CH$_2$CH$_2$N(CH$_3$)$_2$, —NHCH$_2$CH$_2$CH$_2$NH$_2$).

Synthesis of Fluorescently Labeled Polymer 1.

A fluorescently-labeled analog of polymer 1 (Polymer 1$_{TMR}$) was synthesized using the following procedure. Polymer 1 (16.9 mg, 30.7 μmol) was weighed into a screw-capped vial equipped with a magnetic stir bar. DMSO (0.93 mL) and TEA (3.0 μL) were added to the vial and the solution was stirred for four hours at room temperature. TMR-NHS (7.4 mg, 14 μmol) was dissolved in 74 μL of DMSO and added to this solution. The reaction solution was stirred at room temperature for 50 h. The DMSO was removed by maintaining the vial under low pressure at 50° C. for two days. The polymer was isolated by dialysis against DI water (MW cut-off=3500) for three weeks and lyophilized to produce a pink solid that was used without further purification.

Preparation of LC Emulsions.

A dispersion of LC droplets was formed by alternately sonicating a mixture of 5CB in an aqueous buffer (1 vol %; 10 mM HEPES, pH 7.0) for 10 seconds followed by agitation with a vortex mixer for 10 seconds. This process was repeated a minimum of five times. A volume of the LC emulsion (150 μL) was added to a solution of polymer 1 (1:2 v/v, respectively) dissolved in HEPES buffer. The LC emulsion was rotated gently end-over-end using a laboratory rotator for up to 25 hours. Excess polymer solution was removed from the bulk aqueous phase by using the following washing procedure. A dispersion of LC droplets (200 μL) was combined with HEPES buffer (1 mL) in a microcentrifuge tube. The sample was centrifuged for 10 minutes at 500 g. The supernatant was removed and the droplets were resuspended in HEPES buffer (200 μL). Microscopy images of the droplets were collected by placing the dispersion of LC droplets (10 μL) on a glass coverslip (either untreated or modified with multilayered polymer films, see text). For experiments designed to investigate the immobilization of droplets on multilayered films, droplets were allowed to settle to the surface of these substrates for a period of 10 minutes. Freely suspended droplets were then removed from the solution by flowing buffer over the surface using a micropipette at a rate of approximately 20 μL/s.

Layer-by-Layer Fabrication of Polymer Thin Films.

Multilayer films composed of BPEI and PVDMA were fabricated in analogy to previously reported methods (Buck, M. E.; Zhang, J.; Lynn, D. M. Adv. Mater. 2007, 19, 3951;

Breitbach, A. S.; Belgrade, S. K.; Blackwell, H. E.; Lynn, D. M. Biomacromolecules 2009, 10, 1564). Briefly, solutions of BPEI and PVDMA were prepared in acetone (20 mM with respect to the molecular weight of the repeat unit). Glass and silicon substrates were cleaned with deionized water, methanol, ethanol, and acetone and dried under a stream of filtered, compressed air prior to the fabrication of multilayered films.

Films were deposited layer-by-layer on glass or silicon manually according to the following general procedure: 1) Substrates were submerged in a solution of BPEI for 30 seconds, 2) substrates were removed and immersed in an initial acetone bath for 30 seconds followed by a second acetone bath for 30 seconds, 3) substrates were submerged in a solution of PVDMA for 30 seconds, and 4) substrates were rinsed in the manner described above. This cycle was repeated until four layer pairs (or 'bilayers') of BPEI/PVDMA were deposited to yield thin films (approximately 30 nm thick) terminated with a final layer of PVDMA. Films were dried under a stream of filtered, compressed air and were either used immediately or stored in a vacuum desiccator prior to use.

Additional modification of these azlactone-functionalized reactive films to design amine-functionalized or carboxylate-functionalized surfaces was performed by either (i) submerging the substrates into a solution of BPEI for 30 seconds to terminate the film with a final layer of BPEI, followed by rinsing as described above, or (ii) hydrolyzing residual azlactone functionality in the films by placing the substrate in a closed vessel under complete saturation of water vapor at 37° C. for 48 hours. Complete hydrolysis of the residual azlactone functionality was confirmed by PM-IRRAS. To fabricate surfaces with spatially-defined chemical patterns, BPEI/PVDMA films terminated with a final layer of BPEI were treated with a small drop of a PVDMA solution (20 mM in DMSO) for two minutes. Films were then rinsed with cold acetone (approximately −50° C.) and dried under filtered air.

Results and Discussion.

Design and Synthesis of Amphiphilic Polymer 1.

In this study, the inventors designed polymer 1 to include 5 mol % of a primary amine-functionalized side chain to permit conjugation of a fluorescent label and provide a reactive handle for the immobilization of polymer-functionalized LC droplets on amine-reactive surfaces. The ratio of hydrophobic, tertiary amine-functionalized, and primary amine-functionalized side chains in the polymer 1 used in this study was 40:55:5, respectively (see Materials and Methods for additional details related to polymer synthesis and characterization). The chemical structure of Polymer 1 is shown below:

Polymer 1

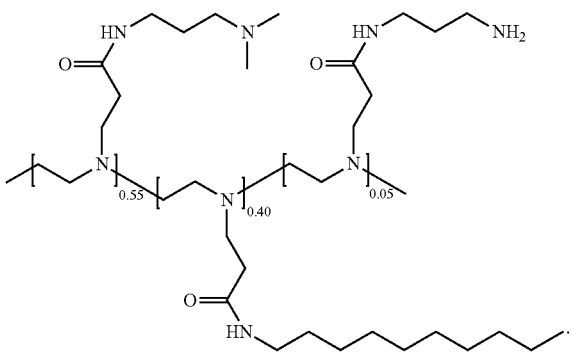

Adsorption of Polymer 1 to LC Emulsion Droplets.

The inventors performed a series of experiments to determine whether polymer 1 could adsorb from bulk aqueous solutions onto the interfaces of dispersed droplets of LC. For these experiments, the inventors sonicated a mixture of the thermotropic LC 5CB and HEPES buffer (1% v/v; pH=7.0) to produce a dispersion of spherical LC droplets. Characterization of this dispersion by optical microscopy revealed approximately 95% of the droplets to be between 1 μm and 8 μm in diameter. The dispersion was then added to a solution of polymer 1 and incubated with continuous and gentle agitation. Samples of this dispersion were removed at various times and characterized by bright-field and polarized light microscopy. The method used to prepare these LC dispersions resulted in a distribution of droplet sizes, and past studies have demonstrated that droplet size can have a strong influence on the ordering of the LC (Gupta, J. K.; Sivakumar, S.; Caruso, F.; Abbott, N. L. Angew. Chem., Int. Ed. 2009, 48, 1652).

With this in mind, the inventors restricted all analyses described here to the characterization of droplets having sizes in the range of 3 μm to 6 μm in diameter. In this part of the study, images of LC droplets were acquired by adjusting the focal plane of the microscope to a position far above the surface of the glass microscope slide to characterize freely moving droplets and minimize the potential influence of contact with the glass slide on the ordering of the LC within the droplets.

FIGS. 1A and 1D show representative bright-field and polarized light micrographs, respectively, of LC droplets in HEPES buffer (i.e., in the absence of polymer). These LC droplets exhibit a so-called bipolar configuration in which the director of the LC is oriented parallel to the surface of the droplets and connects two point defects located at opposite poles of the droplet. FIG. 1G presents a schematic illustration of this director profile. These point defects scatter light, and can thus be observed by bright-field microscopy (e.g., indicated by the white arrows in FIG. 1A). The observation of a bipolar configuration for these droplets is consistent with the behavior of droplets of LC dispersed in aqueous phases reported in other past studies.

The inventors observed large changes in the ordering of LC within droplets incubated in the presence of polymer 1. These changes are exemplified by the bright-field and polarized light micrographs shown in FIGS. 1B, 1C, 1E, and 1F. The images in FIGS. 1B and 1E correspond to droplets incubated in a solution of polymer 1 (at a concentration of 0.1 mg/mL) for two hours. In contrast to the images shown in FIGS. 1A and 1D, these images reveal the presence of a single point defect located at the surface of the droplet (e.g., indicated by the white arrow in FIG. 1B). The presence of this single point defect is consistent with a shift of the orientation of the LC from a bipolar configuration to a so-called preradial configuration, in which the director radiates outward from the single point defect (see FIG. 1H for a schematic illustration).

Because the director profile for the preradial configuration is not spherically symmetric (that is, the point defect is not located in the center of the sphere), the apparent location of the defect changes as the droplet rotates in solution. This characteristic allows this type of defect to be identified easily and distinguished from the so-called radial configuration in which the defect is located in the geometric center of the LC droplet (and, thus, does not move as the droplet rotates; see FIG. 1I for a schematic illustration of this configuration). The inventors observed radial configurations in bright-field images of LC droplets incubated in the presence of higher concentrations of polymer 1 (e.g., 1.0 mg/mL) as shown in FIG. 1C. This radial configuration leads to a characteristic cross-like pattern when viewed under polarized light (FIG. 1F). The preradial and radial configurations shown in FIGS. 1B and 1C, respectively correspond to droplets incubated in solutions of polymer 1 for two hours.

The change from a bipolar configuration to preradial or radial configurations upon exposure of the droplets to polymer 1 is consistent with the adsorption of polymer 1 to the interfaces of the droplets. Past studies using small molecule surfactants with long aliphatic tails have demonstrated that the ordering of LC droplets generally passes through a progression from bipolar, preradial, and radial configurations as the concentration of surfactant in the aqueous phase is increased (Gupta, J. K.; Zimmerman, J. S.; de Pablo, J. J.; Caruso, F.; Abbott, N. L. Langmuir 2009, 25, 9016). The polymer-induced ordering transitions shown in FIG. 1 are consistent with these past results.

Figure 2:
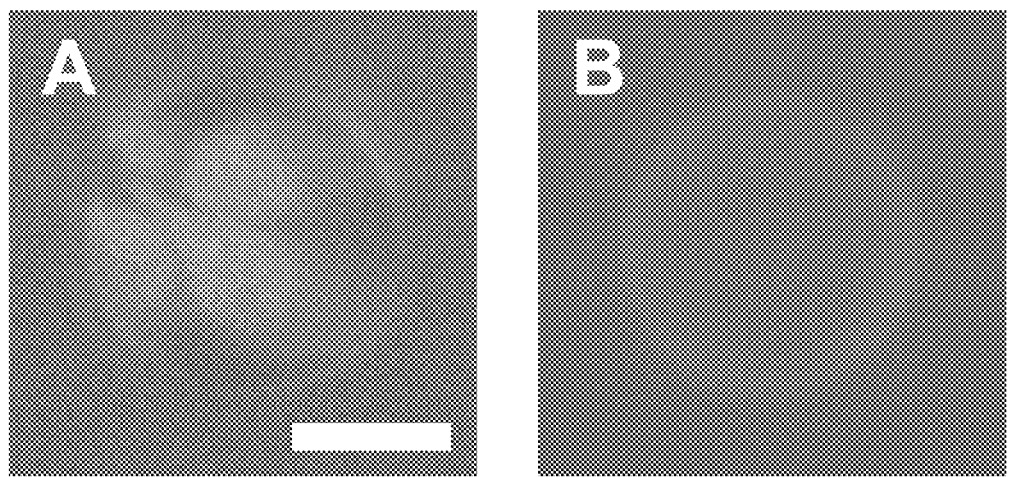
FIG. 2: A) Polarized light and B) fluorescence micrographs of a 5CB droplet dispersed in a mixture of polymer 1 and polymer $1_{TMR}$ (4:1, 0.1 mg/mL) for 2 h. Excess polymer was removed from the bulk aqueous solution prior to imaging. Scale bar=3 μm.

To provide additional evidence of the adsorption of polymer 1 to the interfaces of LC droplets, the inventors performed experiments using a fluorescently labeled analog of polymer 1 (polymer $1_{TMR}$) synthesized by the conjugation of carboxytetramethylrhodamine succinimidyl ester (TMR-NHS) to the primary amine side chains of polymer 1. FIG. 2 shows bright-field and fluorescence microscopy images of a droplet in the preradial configuration incubated in the presence of a polymer 1/polymer $1_{TMR}$ mixture (0.1 mg/mL, 4:1 mass ratio) for two hours. This image shows bright fluorescence distributed over the droplet interface and confirms the presence of polymer on the interface of the droplet. The results of additional characterization of LC droplets coated using polymer $1_{TMR}$ are discussed later in this Example.

Immobilization of LC Droplets on Functional Surfaces.

The results of the experiments described above demonstrate that dispersed 5CB droplets can be decorated with polymers containing amine functionality. The inventors' next experiments sought to determine if they could exploit the primary amine functionality of polymer 1 to immobilize LC droplets on amine-reactive surfaces. The specific approach they investigated here is based on the reactive layer-by-layer assembly of thin films fabricated using poly(2-vinyl-4,4'-dimethylazlactone) (PVDMA) and branched poly(ethylene imine) (BPEI) (Buck, M. E.; Breitbach, A. S.; Belgrade, S. K.; Blackwell, H. E.; Lynn, D. M. Biomacromolecules 2009, 10, 1564).

To test the feasibility of using amine-reactive multilayered films to immobilize LC droplets decorated with polymer 1, the inventors fabricated BPEI/PVDMA thin films four bilayers thick (a 'bilayer' refers to one BPEI/PVDMA layer pair) on the surfaces of glass cover slips. These films were fabricated to present PVDMA as the final, topmost layer of the film and on average, were approximately 30 nm thick (as determined by ellipsometry). These azlactone-functionalized surfaces are referred to hereafter as surface 1 (shown in the schematic illustration in FIG. 3A, see Materials and Methods for additional details related to film fabrication).

Droplets of 5CB were decorated with polymer 1 by dispersing the droplets in a solution of polymer 1 at 0.1 mg/mL for 2 hours, as described above, after which the droplets were separated from the bulk aqueous phase by centrifugation and resuspended in fresh buffer. The polymer-laden 5CB droplets were dispensed onto surface 1 and allowed to sediment onto the surface for approximately 10 minutes before characterization by bright-field and polarized light microscopy. The inventors observed the motion (lateral and rotational) of 5CB droplets to fall qualitatively into three different categories: i) droplets moving rapidly (at rates greater than approximately 1 μm/s), ii) droplets moving slowly (at rates less than approximately 0.1 μm/s), and iii) droplets that were completely immobile. The movement of droplets located far from the surface fell into the first category (i.e., relatively rapid motion) and was driven by a combination of fluid convection and Brownian motion. As the 5CB droplets approached the surface of the multilayers, the movement of the droplets slowed considerably (category two) due to hydrodynamic and other long range interactions until they came into contact with the surface and motion ceased altogether (category three; the ordering of LC within the droplets after contact with the surface will be discussed below). The observation that the motion of polymer-decorated LC droplets ceased when in contact with surface 1 is consistent with the hypothesis that polymer 1-decorated LC droplets can be immobilized on these amine-reactive films.

The inventors characterized qualitatively the strength of the interactions between polymer 1-decorated LC droplets and surface 1 (e.g., whether droplets were bound weakly or strongly to these surfaces) by attempting to remove the droplets from the surfaces through rinsing. FIG. 3 shows polarized light micrographs captured from the same field of view before (FIG. 3B) and after (FIG. 3C) rinsing immobilized LC droplets with solutions of fresh buffer at a rate of approximately 20 μL/s. These images reveal that the rinsing process did not change the number or location of the droplets immobilized on the multilayers and suggest that the interactions between the droplets and surface 1 are sufficiently strong to hold the droplets at surface 1 when exposed to flowing buffer To gain additional insight into the nature of the interactions between polymer 1-coated LC droplets and the azlactone groups of surface 1, the inventors designed two additional surfaces displaying different chemical functionality. The first of these two additional surfaces, surface 2, was prepared by depositing one additional layer of BPEI onto the 4-bilayer films of BPEI and PVDMA (as described above). The addition of a final layer of BPEI was designed to mask the azlactone groups and increase the amount of amine functionality present at the surface of the film (schematic illustration shown in FIG. 3G). The second of these additional surfaces, surface 3, was prepared by treating 4-bilayer BPEI/PVDMA films with saturated water vapor (48 hours at 37° C.) to hydrolyze residual azlactone functionality remaining within the film after fabrication of the multilayers and generate carboxylic acid functionality (see the schematic illustration in FIG. 3J). Complete hydrolysis of the residual azlactone groups in these films was confirmed by reflective infrared spectroscopy (data not shown).

In analogy to the experiments described above, dispersions of polymer 1-coated droplets of 5CB were dispensed onto surfaces 2 and 3, the droplets were allowed to sediment onto the surfaces, and the samples were vigorously rinsed with solutions of fresh buffer. When polymer-coated droplets were placed on surface 2, the droplets continued to move freely during sedimentation and were completely displaced from the surface upon rinsing (FIGS. 3H and 3I), suggesting that the additional layer of BPEI was sufficient to prevent immobilization of the droplets on azlactone-containing multilayers. In contrast, polymer-coated LC droplets became immobile after coming into contact with surface 3 and were not removed by the rinsing process (FIGS. 3K and 3L). These results show that non-covalent associations (e.g., electrostatic interactions) between polymer 1-coated droplets and hydrolyzed PVDMA multilayers were sufficiently strong to immobilize the LC droplets on these surfaces.

To investigate further the nature of the immobilization of polymer 1-coated LC droplets on surface 1 and surface 3, immobilized droplets were rinsed with a buffer solution of high ionic strength. If the interactions between the surfaces and the droplets were primarily electrostatic in nature (e.g., between carboxylates at the surfaces and protonated amines of polymer 1), a high concentration of salt would screen these interactions and potentially result in the release of the droplets from the surfaces. The images shown FIGS. 3D and 3M were captured immediately after rinsing polymer-coated LC droplets immobilized on surface 1 or surface 3, respectively, with buffer solutions (10 mM HEPES, pH 7.0) containing 1.5 M NaCl (at a rate of approximately 20 µL/s). LC droplets on surface 1 were undisturbed by the additional rinse (FIG. 3D) whereas LC droplets on surface 3 were completely rinsed from the film by the high ionic strength solution (FIG. 3M). These results provide evidence that electrostatic forces are responsible for the immobilization of the droplets to the surfaces of hydrolyzed PVDMA multilayers (surface 3).

The observation that LC droplets on surface 1 were not dislodged after treatment with high salt concentrations is consistent with the view that the polymer-decorated LC droplets are covalently immobilized on surface 1 as a result of ring-opening reactions between the primary amine functionality of polymer 1 and the azlactone groups in these films. Although reaction between the primary amines of polymer 1 adsorbed to LC droplets and the azlactone functionality presented on surface 1 could not be confirmed spectroscopically because of the physical constraints of this system, the results shown in FIGS. 3B-D suggest that the interactions between polymer 1-coated droplets and surface 1 are covalent in nature.

Finally, to establish that the immobilization of the droplets on surface 1 was a result of the presence of polymer 1 on the interfaces of the droplets and not a consequence of interactions between the surface and 5CB alone, the experiments described above were repeated using a dispersion of uncoated LC droplets. Uncoated droplets were dispensed onto surface 1 and allowed to sediment onto the film surface (FIG. 3E). The droplets were completely flushed from the films after rinsing with buffer (10 mM HEPES, pH 7.0) as shown in FIG. 3F. This result demonstrates that polymer 1 is necessary to immobilize the LC droplets on azlactone-containing multilayers. On the basis of the results described above and illustrated in FIG. 3, one can see that reactive multilayered films terminated with a layer of PVDMA can be used to immobilize LC droplets coated with amphiphilic polyamines such as polymer 1.

Ordering of LC Droplets Immobilized on Surfaces.

As discussed above, polymer 1-laden 5CB droplets prepared and suspended in bulk aqueous solution ([polymer 1]=0.1 mg/mL, 2 hours of incubation) exhibited a preradial configuration (FIGS. 1B, 1E, and 1H). In the experiments using multilayered films described above, the inventors observed that when polymer 1-laden 5CB droplets came into contact with surface 1, a change in the ordering of the LC occurred.

FIG. 4A shows a bright-field image of a polymer-laden 5CB droplet freely moving in the bulk prior to coming into direct contact with surface 1. A single characteristic point defect resides on the outer edge of the droplet, consistent with a preradial configuration. FIG. 4B shows an image of the same droplet after contacting surface 1. The point defect immediately (in less than 1 second) migrated to the center of the droplet (as viewed from above) upon surface contact. The location of this defect did not change measurably when these surfaces were rinsed to remove unbound LC droplets.

To determine the out-of-plane location of the point defect, the inventors adjusted the focal plane of the microscope to focus on different horizontal sections of the droplets. The micrographs in FIGS. 5A-D correspond to bright-field (5A and 5B) and polarized light (5C and 5D) images of a polymer-laden droplet on surface 1 with the focal plane adjusted at approximately the midpoint of the droplet (FIGS. 5A and 5C) to approximately at the apex of the droplet (FIGS. 5B and 5D). Inspection of these images reveals that the point defect is in the same approximate focal plane as the widest point of the outer droplet edge and suggests that the point defect is located near the midpoint of the droplet. This defect structure is consistent with the radial ordering configuration.

Figure 4:
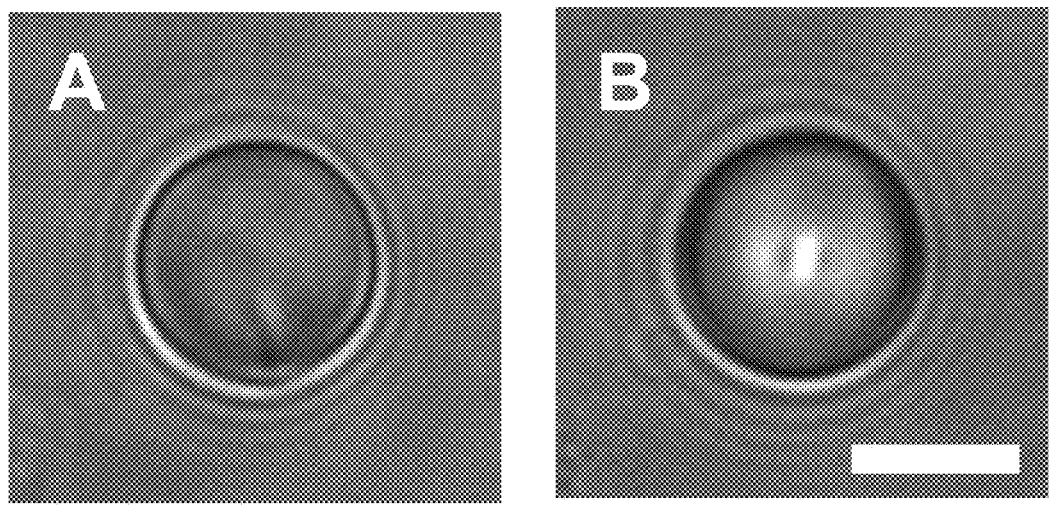
FIG. 4: A) Bright-field micrograph of a polymer 1-laden 5CB droplet freely moving above a multilayer film presenting azlactone functionality (surface 1). B) Bright-field micrograph of the same 5CB droplet after contacting the surface of the film (immobile). Scale bar=5 μm.

When mobile polymer 1-laden droplets contacted surface 3, the point defect was also observed to migrate from the edge to the center of the droplet (as viewed from above), similar to the result shown in FIG. 4 for droplets contacting surface 1. However, adjustment of the focal plane of the microscope from the midpoint of the droplet (FIGS. 5E and 5G) to the apex of the droplet (FIGS. 5F and 5H) demonstrated that the defect was located near the apex. This defect structure, distinct from droplets immobilized on surface 1, is consistent with the preradial ordering configuration similar to the ordering of freely-moving droplets before contact with surface 3. The ordering of these droplets immobilized on surface 3 differs however, from freely-moving droplets in that the location of the point defect remained as the apex of the droplet. As discussed above, the apparent location of the point defect of mobile droplets changes as the droplet rotates in solution.

In addition, close inspection of FIGS. 5G and 5H revealed the appearance of a twist distortion within the defect structure of the droplet immobilized on surface 3 that was not observed for droplets on immobilized surface 1 (FIG. 5C). Previous studies have reported twisted director configurations in LC droplets in cases with perpendicular alignment at the droplet surface, and theoretical consideration of the twisted configurations observed in these past studies suggested that they arise from a combination of the drop size and the Frank elastic constants for different modes of elastic deformation (the elastic constant for twist is less than splay and bend deformations) (Rudinger, A.; Stark, H. *Liq. Cryst.* 1999, 26, 753).

The ordering of LCs in contact with surfaces can be influenced by a number of different factors, including the chemistry or topography of the surface. In the context of this Example, immobilization of polymer 1-decorated 5CB droplets on polymeric films triggers ordering transitions in the LCs that are dependent on the nature of the chemical functionality and post-fabrication modification of the multilayered films.

Characterization of the Shapes of Droplets Immobilized on Surfaces.

Figure 6:
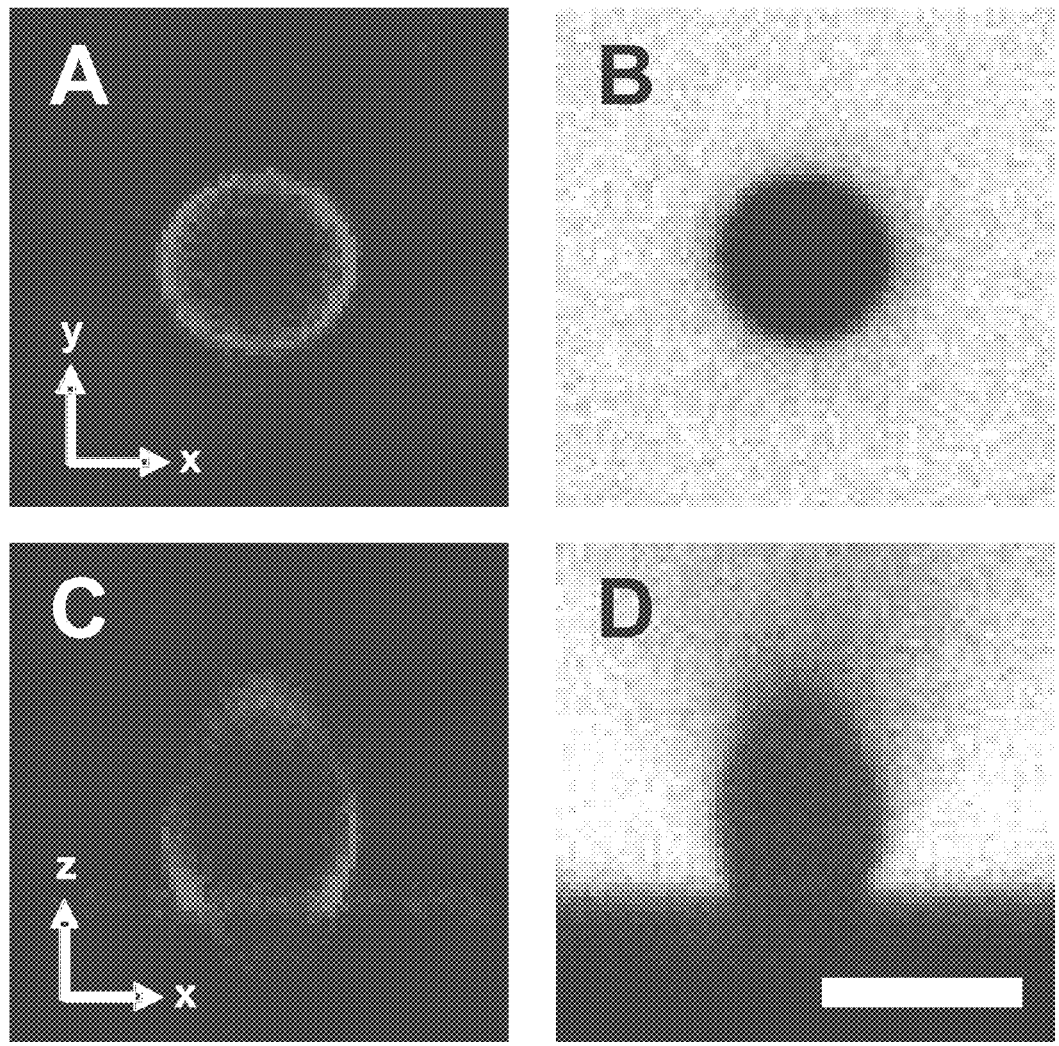
FIG. 6: Confocal fluorescence micrographs of a polymer-laden LC droplet immobilized on surface 1 captured in the (A, B) x-y plane (bottom-up view) or the (C, D) x-z plane (side-on view). Images were captured by collecting the red channel (A, C; polymer $1_{TMR}$ adsorbed to the surface of the LC droplets) or the green channel (B, D; FITC-dextran dispersed in the aqueous solution). Scale bar=5 μm.

The inventors considered the possibility that the changes in ordering of the polymer-laden LC droplets shown in FIG. 5 may be driven by changes or differences in the shapes of the droplets as they contact surface 1 or surface 3. The next experiments sought to characterize the shapes of immobilized 5CB droplets and determine if, and to what extent, their shapes change after contact with BPEI/PVDMA multilayers using laser scanning confocal microscopy (LSCM). For these experiments, droplets of 5CB were coated with polymer $1_{TMR}$ (using a procedure analogous to the coating of droplets with polymer 1 described above) and allowed to sediment onto surface 1. After the polymer-laden droplets sedimented to the surface of the films, the aqueous phase was exchanged with a solution of FITC-labeled dextran (10 mg/mL in HEPES buffer). The images shown in FIG. 6 are representative LSCM images of a single LC droplet captured in the x-y plane (i.e., bottom-up view of droplet; FIGS. 6A and 6B) or in the x-z plane (i.e., a cross-sectional side view of the droplet; FIGS. 6C and 6D). FIGS. 6A and 6C are the result of collecting fluorescence from the red channel and reveal a ring of bright red intensity corresponding to polymer $1_{TMR}$ adsorbed to interface of the droplet. Independent collection of fluorescence from the green channel (FIGS. 6B and 6D) provided an additional view of the droplet. In these images, the regions of bright green intensity correspond to the FITC-labeled dextran dispersed throughout the aqueous solution.

A comparison of the series of images shown in FIG. 6 reveals that both approaches to characterizing the immobilized droplet (imaging polymer $1_{TMR}$ on the droplet interface or a fluorescence dye distributed throughout the aqueous solution) lead to similar conclusions regarding the droplet shapes. Further inspection of FIGS. 6C and 6D indicates that the droplets exhibited contact angles of at least 90° on the surface. Additional control experiments using rigid glass beads revealed that the elongated distortion in the top half of these images arises from optical effects associated with imaging (data not shown), and thus the droplets should not be interpreted to be egg-like in shape. Therefore, conclusions from these experiments are limited to observations made of the bottom half of these images, and no conclusions are drawn regarding differences in the distribution of polymer $1_{TMR}$ on the interface of the 5CB droplets.

In an analogous set of experiments, LSCM was used to characterize the shape of polymer $1_{TMR}$-coated 5CB droplets immobilized on surface 3. No significant difference between the general shape of the droplets on surface 1 (as shown in FIG. 6) and surface 3 (data not shown) was observed. In summary, these results demonstrate that the surface-dependent LC ordering transitions shown in FIGS. 4 and 5 were not a consequence of large differences in the shapes of the droplets immobilized on surface 1 or surface 3.

Patterning of LC Droplets on Azlactone-Functionalized Surfaces.

The experiments described above demonstrate that 5CB droplets decorated with polymer 1 can be immobilized on multilayers terminated with PVDMA and that films terminated in BPEI resist the adhesion or immobilization of the droplets. In a final set of experiments, the inventors sought to determine whether the multilayered films could be chemically patterned in a manner that would provide spatial control over the immobilization of LC droplets.

For the experiments described here, a BPEI-terminated film (3.5 bilayers thick) was treated with a small drop (0.5 µL) of a solution of PVDMA dissolved in DMSO (20 mM with respect to repeat unit) for 2 minutes, followed by rinsing with acetone to remove excess unreacted PVDMA and the DMSO from the surface. A dispersion of polymer 1-coated LC droplets was then dispensed onto the films and the droplets were allowed to sediment to the surface before rinsing with buffer (10 mM HEPES, pH 7.0) to remove any non-immobilized droplets.

Figure 7:
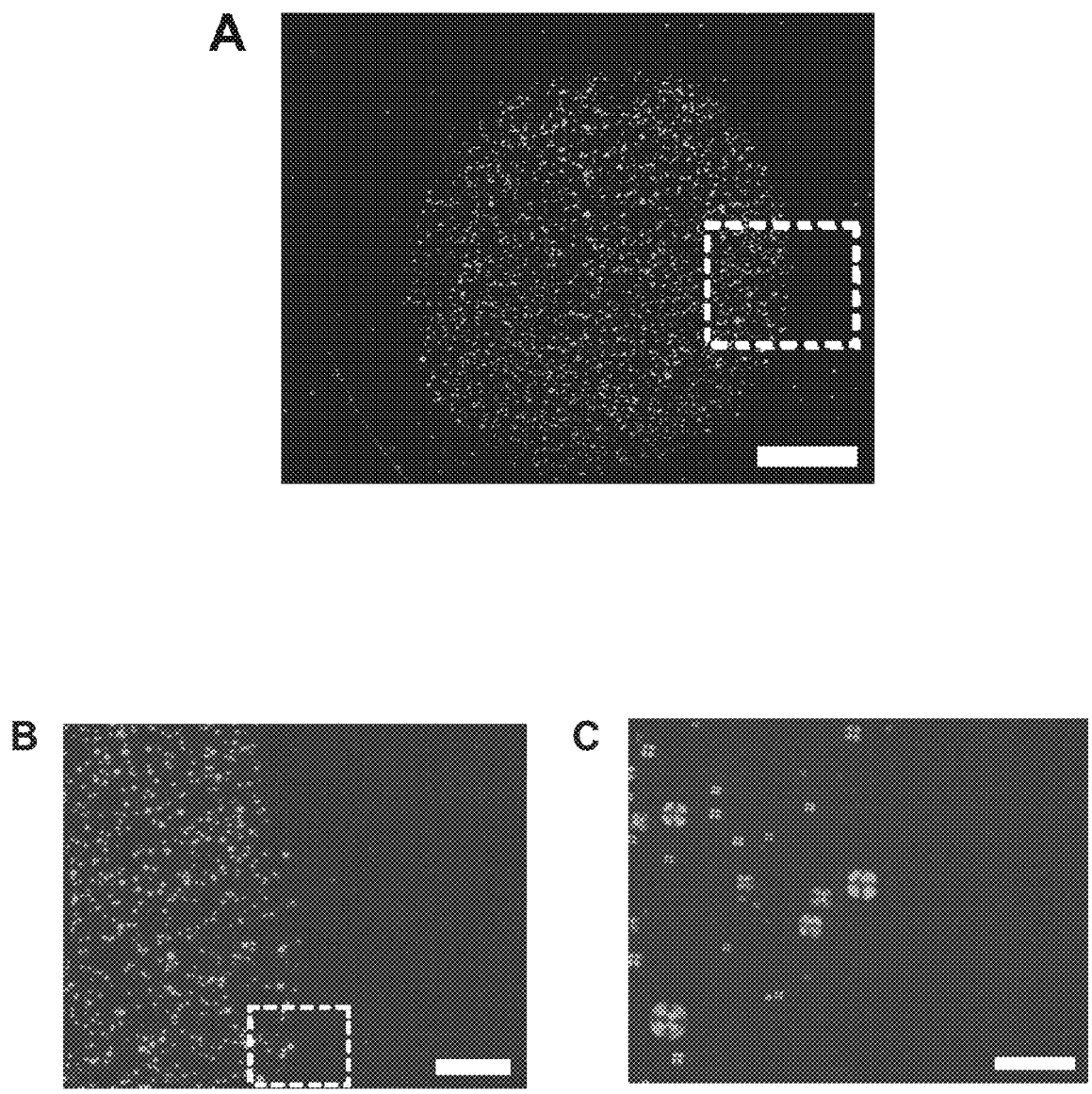
FIG. 7: Polarized light micrograph of polymer 1-coated 5CB droplets on a multilayer film terminated with a layer of BPEI (i.e., surface 2) and patterned with circular region of PVDMA. The dashed boxes in A) and B) correspond to magnified regions shown in B) and C), respectively. See text for additional details. Scale bars=A) 400 μm, B) 100 μm, and C) 20 μm.

FIG. 7A shows a polarized light micrograph of the entire patterned region of the film and FIGS. 7B and 7C are images collected at higher magnification of the boundary between the treated and untreated regions. The broader distribution of droplet sizes produced by the methods used to form the emulsion droplets (as discussed above) can be observed in these images. Inspection of FIG. 7 reveals that the droplets are immobilized on the film surface primarily within the circular area that was treated with PVDMA and that the droplets are largely excluded from the surrounding BPEI terminated film. Although this patterned surface was fabricated using a slightly different approach than the approaches used to fabricate surface 1 and surface 3, the results shown in FIG. 7 are consistent with the results of the experiments illustrated in FIG. 3. These results demonstrate that it is possible to immobilize LC droplets within spatially-defined regions and provide a basis for the patterning of LC droplets on surfaces using other surface-patterning techniques.

SUMMARY AND CONCLUSIONS

In this Example, the inventors have reported the design of an amphiphilic polyamine that can adsorb to the interface of LC droplets dispersed in aqueous solutions. A change in the ordering of the LC (i.e., a transition from a bipolar configuration to a preradial or radial configuration) and the observation of fluorescence around the perimeter of the droplets, when a fluorescently labeled analog of polymer 1 was used, provided evidence that the polymer adsorbed to the interface of the LC droplets. The inventors also demonstrated that polymer 1-decorated 5CB droplets could be immobilized on surfaces coated with chemically tailored polymer multilayers. The results show that the polymer-coated LC droplets can be immobilized on surfaces coated with these multilayered films by either i) covalent bonds (e.g., formed between azlactone functionality presented on surface 1 and primary amine functionality on polymer 1), or ii) electrostatic interactions (e.g., between carboxylate groups on surface 3 and the polyamines adsorbed to the droplets). Immobilization of the LC droplets triggered changes in the ordering of the LCs that were dependent on the chemical functionality presented on the surface of the multilayers.

The inventors further demonstrated that polymer-coated LC droplets could be selectively immobilized within spatially defined patterns. The ability to engineer the properties of LC droplets with amphiphilic polymers may enable a range of fundamental studies on LCs in confined geometries and provide new methods to report on the presence of chemical or biological agents based on immobilized droplets of LCs (for example, through the design of arrays of surface-immobilized LC droplets that undergo analyte-induced changes in defect structure or other properties).

Those skilled in the art will recognize, or be able to ascertain using no more than routine experimentation, numerous equivalents to the specific materials and methods described herein. Such equivalents are considered to be within the scope of this invention and encompassed by the following claims.

We claim:

1. An immobilized liquid-based device, comprising:
   (a) one or more liquid microdomains having a minor axis of between about 0.5 µm and about 1000 µm, the microdomains further comprising a multifunctional polymer,
   (b) a functionalized substrate surface comprising one or more functional groups capable of forming a covalent bond or an electrostatic attraction to the multifunctional polymer, and
   (c) a covalent bond or an electrostatic attraction between the multifunctional polymer and the one or more functional groups of the functionalized substrate surface that directly binds the one or more liquid microdomains to the functionalized substrate surface.

2. The immobilized liquid-based device of claim 1, wherein a covalent bond is formed between the multifunctional polymer and the one or more functional groups of the functionalized substrate surface.

3. The immobilized liquid-based device of claim 1, wherein the liquid microdomains are directly bound to the functionalized substrate with sufficient strength such that the liquid microdomains remain bound to the functionalized substrate surface when the functionalized substrate surface is rinsed with a pH 7 buffer solution at a flow rate of about 20 mL/s.

4. The immobilized liquid-based device of claim 1, wherein the liquid microdomains are comprised of an isotropic oil or a liquid crystal.

5. The immobilized liquid-based device of claim 4, wherein the liquid microdomains are liquid crystal droplets.

6. The immobilized liquid-based device of claim 1, wherein the multifunctional polymer is a polyamine.

7. The immobilized liquid-based device of claim 6, wherein the polyamine includes a side chain functionalized with a primary amine.

8. The immobilized liquid-based device of claim 7, wherein the polyamine further includes a side chain terminating with an aliphatic alkyl moiety of at least five carbons in length.

9. The immobilized liquid-based device of claim 1, wherein the functionalized substrate surface comprises a chemical functionalization layer.

10. The immobilized liquid-based device of claim 9, wherein the functionalized substrate surface is a solid surface coated with a chemically functionalized polymer multilayer.

11. The immobilized liquid-based device of claim 10, wherein the chemically functionalized polymer multilayer is functionalized by one or more of a terminal azlactone moiety, a terminal carboxylic acid moiety, or a terminal carboxylate moiety.

12. The immobilized liquid-based device of claim 10, wherein the outermost layer of the chemically functionalized polymer multilayer is fabricated to cover less than the entire functionalized substrate surface.

13. The immobilized liquid-based device of claim 10, wherein the chemically functionalized polymer multilayer is comprised of one or more bilayers.

14. The immobilized liquid-based device of claim 10, wherein a covalent bond is formed between the multifunctional polymer and the chemically functionalized polymer multilayer.

15. The immobilized liquid-based device of claim 9, wherein the directly bound microdomains form a pattern that corresponds to the spatial placement of the chemical functionalization layer or components thereof on the functionalized substrate surface.

16. The immobilized liquid-based device of claim 15, wherein an electrostatic attraction is formed between the multifunctional polymer and the chemically functionalized polymer multilayer.

17. A method of using an immobilized liquid-based device to detect a target analyte comprising:
(a) providing an immobilized liquid-based device according to claim 1;
(b) contacting the device with a test sample; and
(c) analyzing the liquid microdomains that are directly bound to the functionalized surface, wherein a change in a measurable property of the liquid within the microdomains indicates the presence of the target analyte in the test sample.

18. The method of claim 17, wherein the liquid microdomains that are directly bound to the functionalized surface are comprised of liquid crystal, and wherein the change in a measurable property of the liquid is a change in the orientation or phase of the liquid crystal.

19. A method of using an immobilized liquid-based device to detect a target analyte comprising:
(a) contacting one or more liquid microdomains having a minor axis of between about 0.5 μm and about 1000 μm with a test sample;
(b) directly binding the microdomains to a functionalized substrate surface comprising one or more functional groups by one or both of a covalent bond or an electrostatic attraction between a multifunctional polymer incorporated into the liquid microdomains and the one or more functional groups on the functionalized substrate surface; and
(c) analyzing the liquid microdomains that are directly bound to the functionalized substrate surface, wherein a change in a measurable property of the liquid within the microdomains indicates the presence of the target analyte in the test sample.

20. The method of claim 19, wherein the liquid microdomains that are directly bound to the functionalized substrate surface are comprised of liquid crystal, and wherein the change in a measurable property of the liquid is a change in the orientation or phase of the liquid crystal.

21. A method for spatially or temporally controlling the release or production of an active compound of interest comprising:
(a) providing one or more liquid microdomains comprising a multifunctional polymer and one or more compounds of interest or one or more compounds that are capable of reacting to form a compound of interest, wherein the microdomains have a minor axis of between about 0.5 μm and about 1000 μm,
(b) directly binding the liquid microdomains to a functionalized substrate surface comprising one or more functional groups by one or both of a covalent bond or an electrostatic attraction between the multifunctional polymer and the one or more functional groups on the functionalized substrate surface, and
(c) disrupting the liquid microdomains to release the contents of the liquid microdomains to the surrounding environment.

22. An immobilized liquid-based device, comprising:
(a) one or more liquid microdomains having a minor axis of between about 0.5 μm and about 1000 μm, the microdomains further comprising a multifunctional polymer, and
(b) a substrate surface on which the microdomains are immobilized by one or both of a covalent bond or a non-covalent attraction between the multifunctional polymer and the substrate surface;
wherein the multifunctional polymer has the chemical formula:

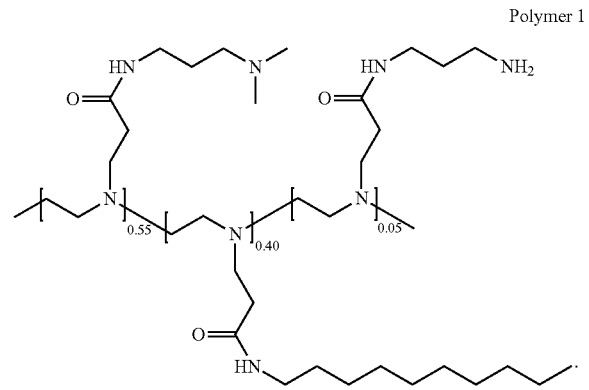

Polymer 1

* * * * *